United States Patent
Hanson et al.

(10) Patent No.: US 7,018,416 B2
(45) Date of Patent: Mar. 28, 2006

(54) BONE IMPLANTS AND METHODS

(75) Inventors: David A. Hanson, St. Louis Park, MN (US); Ross A. Longhini, West Lakeland, MN (US); Daniel D. McPhillips, Ham Lake, MN (US); Steven J. Seme, Savage, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 254 days.

(21) Appl. No.: 10/080,375

(22) Filed: Feb. 19, 2002

(65) Prior Publication Data

US 2003/0028197 A1    Feb. 6, 2003

Related U.S. Application Data

(63) Continuation-in-part of application No. 09/896,926, filed on Jun. 28, 2001, now Pat. No. 6,635,060, which is a continuation-in-part of application No. 09/611,237, filed on Jul. 6, 2000, now Pat. No. 6,641,582.

(60) Provisional application No. 60/269,777, filed on Feb. 16, 2001.

(51) Int. Cl.
*A61F 2/44* (2006.01)

(52) U.S. Cl. ................................. 623/17.16
(58) Field of Classification Search ............ 623/17.11, 623/17.12, 17.13, 17.14, 17.15, 17.16, 23.51, 623/23.6, 23.61, 23.63, 23.76; 606/61, 76
See application file for complete search history.

(56) References Cited

U.S. PATENT DOCUMENTS

| | | | |
|---|---|---|---|
| 3,848,601 A | 11/1974 | Ma et al. | |
| 3,867,728 A | 2/1975 | Stubstad et al. | |
| 4,743,256 A | 5/1988 | Brantigan | |
| 4,834,757 A | 5/1989 | Brantigan | |
| 4,877,020 A | 10/1989 | Vich | |
| 4,878,915 A | 11/1989 | Brantigan | |
| 4,904,261 A | 2/1990 | Dove et al. | |
| 4,950,296 A * | 8/1990 | McIntyre | ................ 623/23.63 |
| 5,015,247 A | 5/1991 | Michelson | |
| 5,084,050 A | 1/1992 | Draenert | |
| 5,112,354 A | 5/1992 | Sires | |
| 5,147,402 A | 9/1992 | Bohler et al. | |
| 5,151,104 A | 9/1992 | Kenna | |

(Continued)

FOREIGN PATENT DOCUMENTS

EP    0 425 542 B1    5/1991

(Continued)

OTHER PUBLICATIONS

Branch Jr., M.D , Charles L.; Surgical Technique Manual for the "Tangent™ Posterior Discectomy & Grafting Instrumentation Set" Medtronic Sofamor Danek, publisher.

(Continued)

*Primary Examiner*—David O. Reip
(74) *Attorney, Agent, or Firm*—Faegre & Benson LLP

(57) ABSTRACT

Implants, instruments and methods for bone fusion procedures are disclosed. In some embodiments, the implants are particularly advantageous for use between opposing vertebral bodies to facilitate stabilization or arthrodesis of an intervertebral joint. The implants include, at least, a support component that provides structural support during fusion. In a typical embodiment, the implants also include a growth component. A growth component provides an environment conducive to new bone growth between the bones being fused. Several unique configurations to enhance fusion, instruments for insertion and methods for insertion are also disclosed.

22 Claims, 20 Drawing Sheets

U.S. PATENT DOCUMENTS

| | | |
|---|---|---|
| 5,192,327 A | 3/1993 | Brantigan |
| 5,298,254 A | 3/1994 | Prewett et al. |
| 5,306,302 A | 4/1994 | Bauer et al. |
| 5,397,364 A | 3/1995 | Kozak et al. |
| 5,425,772 A | 6/1995 | Brantigan |
| 5,439,684 A | 8/1995 | Prewett et al. |
| 5,443,514 A | 8/1995 | Steffee |
| 5,496,371 A | 3/1996 | Eppley et al. |
| 5,514,180 A | 5/1996 | Heggeness et al. |
| 5,522,899 A | 6/1996 | Michelson |
| 5,571,109 A | 11/1996 | Bertagnoli |
| 5,585,116 A | 12/1996 | Boniface et al. |
| 5,593,409 A | 1/1997 | Michelson |
| 5,609,635 A | 3/1997 | Michelson |
| 5,609,636 A | 3/1997 | Kohrs et al. |
| 5,609,637 A | 3/1997 | Biedermann et al. |
| 5,645,598 A | 7/1997 | Brosnahan, III |
| 5,645,599 A * | 7/1997 | Samani ............... 623/17.16 |
| 5,653,762 A | 8/1997 | Pisharodi |
| 5,658,336 A | 8/1997 | Pisharodi |
| 5,658,337 A | 8/1997 | Kohrs et al. |
| 5,669,909 A | 9/1997 | Zdeblick et al. |
| 5,676,146 A | 10/1997 | Scarborough |
| 5,702,449 A | 12/1997 | McKay |
| 5,713,899 A | 2/1998 | Marnay et al. |
| 5,716,415 A | 2/1998 | Steffee |
| 5,722,977 A | 3/1998 | Wilhelmy |
| 5,728,159 A | 3/1998 | Stroever et al. |
| 5,733,288 A | 3/1998 | Allen |
| 5,741,253 A | 4/1998 | Michelson |
| 5,741,261 A | 4/1998 | Moskovitz et al. |
| 5,769,897 A | 6/1998 | Härle |
| 5,776,199 A | 7/1998 | Michelson |
| 5,782,830 A | 7/1998 | Farris |
| 5,785,710 A | 7/1998 | Michelson |
| 5,797,909 A | 8/1998 | Michelson |
| 5,814,084 A | 9/1998 | Grivas et al. |
| 5,865,845 A | 2/1999 | Thalgott |
| 5,868,749 A | 2/1999 | Reed |
| 5,885,292 A | 3/1999 | Moskovitz et al. |
| 5,888,219 A | 3/1999 | Bonutti |
| 5,888,222 A | 3/1999 | Coates et al. |
| 5,888,227 A | 3/1999 | Cottle |
| 5,888,228 A | 3/1999 | Knothe et al. |
| 5,891,147 A | 4/1999 | Moskovitz et al. |
| 5,893,890 A | 4/1999 | Pisharodi |
| 5,895,426 A | 4/1999 | Scarborough et al. |
| 5,899,939 A | 5/1999 | Boyce et al. |
| 5,916,216 A | 6/1999 | DeSatnick et al. |
| 5,968,047 A | 10/1999 | Reed |
| 5,972,368 A | 10/1999 | McKay |
| 5,989,289 A | 11/1999 | Coates et al. |
| 6,025,538 A | 2/2000 | Yaccarino, III |
| 6,033,438 A | 3/2000 | Bianchi et al. |
| 6,056,749 A | 5/2000 | Kuslich |
| 6,059,790 A | 5/2000 | Sand et al. |
| 6,063,088 A | 5/2000 | Winslow |
| 6,066,174 A | 5/2000 | Farris |
| 6,096,080 A | 8/2000 | Nicholson et al. |
| 6,096,081 A | 8/2000 | Grivas et al. |
| 6,111,164 A | 8/2000 | Rainey et al. |
| 6,143,033 A | 11/2000 | Paul et al. |
| 6,159,245 A | 12/2000 | Meriwether et al. |
| 6,174,311 B1 | 1/2001 | Branch et al. |
| 6,193,755 B1 | 2/2001 | Metz-Stavenhagen et al. |
| 6,200,347 B1 | 3/2001 | Anderson et al. |
| 6,203,544 B1 | 3/2001 | Gotzen |
| 6,206,922 B1 | 3/2001 | Zdeblick et al. |
| 6,206,923 B1 | 3/2001 | Boyd et al. |
| 6,224,599 B1 | 5/2001 | Baynham et al. |
| 6,251,140 B1 | 6/2001 | Marino et al. |
| 6,258,125 B1 | 7/2001 | Paul et al. |
| 6,261,586 B1 | 7/2001 | McKay |
| 6,270,528 B1 | 8/2001 | McKay |
| 6,277,149 B1 | 8/2001 | Boyle et al. |
| 6,302,914 B1 | 10/2001 | Michelson |
| 6,315,795 B1 | 11/2001 | Scarborough et al. |
| 6,395,034 B1 * | 5/2002 | Suddaby .............. 623/17.15 |
| 6,468,311 B1 | 10/2002 | Boyd et al. |
| 6,530,955 B1 * | 3/2003 | Boyle et al. .......... 623/17.11 |
| 6,558,424 B1 | 5/2003 | Thalgott |
| 6,562,073 B1 * | 5/2003 | Foley ................. 623/17.11 |
| 6,706,067 B1 * | 3/2004 | Shimp et al. ........ 623/17.11 |
| 2001/0031254 A1 | 10/2001 | Bianchi et al. |
| 2002/0016633 A1 * | 2/2002 | Lin et al. ............ 623/17.11 |
| 2002/0045944 A1 * | 4/2002 | Muhanna et al. ..... 623/17.16 |
| 2002/0106393 A1 | 8/2002 | Bianchi et al. |
| 2002/0128717 A1 | 9/2002 | Alfaro et al. |
| 2003/0060825 A1 * | 3/2003 | Alfaro et al. ............ 606/61 |
| 2004/0088055 A1 * | 5/2004 | Hanson et al. ....... 623/17.16 |

FOREIGN PATENT DOCUMENTS

| | | |
|---|---|---|
| EP | 0 577 179 A1 | 1/1994 |
| EP | 0 627 204 A2 | 12/1994 |
| EP | 0 637 439 A1 | 2/1995 |
| EP | 0 646 366 A1 | 4/1995 |
| EP | 0 716 840 A2 | 6/1996 |
| EP | 0 732 093 A2 | 9/1996 |
| EP | 0 734 702 A1 | 10/1996 |
| EP | 0 734 703 A2 | 10/1996 |
| EP | 0 646 366 B1 | 12/1997 |
| EP | 0 824 893 A2 | 2/1998 |
| EP | 0 853 932 A2 | 7/1998 |
| EP | 0 880 938 A1 | 12/1998 |
| EP | 1 104 665 A1 | 6/2001 |
| JP | 8126647 | 5/1996 |
| WO | WO 90/00037 | 1/1990 |
| WO | WO 94/05235 | 3/1994 |
| WO | WO 95/08306 | 3/1995 |
| WO | WO 95/08964 | 4/1995 |
| WO | WO 95/22946 | 8/1995 |
| WO | WO 96/40014 | 12/1996 |
| WO | WO 97/14377 | 4/1997 |
| WO | WO 97/14378 | 4/1997 |
| WO | WO 97/23175 | 7/1997 |
| WO | WO 97/25945 | 7/1997 |
| WO | WO 97/32547 | 9/1997 |
| WO | WO 98/17209 | 4/1998 |
| WO | WO 98/38924 | 9/1998 |
| WO | WO 98/44877 | 10/1998 |
| WO | WO 98/48738 | 11/1998 |
| WO | WO 98/56319 | 12/1998 |
| WO | WO 99/09914 | 3/1999 |
| WO | WO 99/49818 | 10/1999 |
| WO | WO 99/56676 | 11/1999 |
| WO | WO 00/07527 | 2/2000 |
| WO | WO 00/07528 | 2/2000 |
| WO | WO 00/24327 | 5/2000 |
| WO | WO 00/25707 | 5/2000 |
| WO | WO 00/40177 | 7/2000 |
| WO | WO 00/40179 | 7/2000 |
| WO | WO 00/41654 A3 | 7/2000 |
| WO | WO 00/42954 | 7/2000 |
| WO | WO 00/44318 | 8/2000 |
| WO | WO 00/44320 | 8/2000 |
| WO | WO 00/45753 | 8/2000 |
| WO | WO 00/74607 A1 | 12/2000 |
| WO | WO 00/74608 A1 | 12/2000 |
| WO | WO 01/08611 A1 | 2/2001 |
| WO | WO 01/08714 A1 | 2/2001 |
| WO | WO 01/28465 A3 | 4/2001 |
| WO | WO 01/28469 A3 | 4/2001 |
| WO | WO 01/32110 A2 | 5/2001 |

| | | |
|---|---|---|
| WO | WO 01/43620 A2 | 6/2001 |
| WO | WO 01/49219 A1 | 7/2001 |
| WO | WO 01/49220 A1 | 7/2001 |
| WO | WO 01/54629 A1 | 8/2001 |
| WO | WO 01/62191 A2 | 8/2001 |
| WO | WO 01/66048 A1 | 9/2001 |
| WO | WO 01/68005 A2 | 9/2001 |
| WO | WO 01/70137 A2 | 9/2001 |
| WO | WO 01/82844 A2 | 11/2001 |
| WO | WO 02/02151 A2 | 1/2002 |
| WO | WO 02/03867 A2 | 1/2002 |

OTHER PUBLICATIONS

"Tangent™ Posterior Discectomy & Grafting Instrumentation Set: Surgical Technique," *Medtronic Sofamor Danek*, 26 pgs. (1999).

* cited by examiner

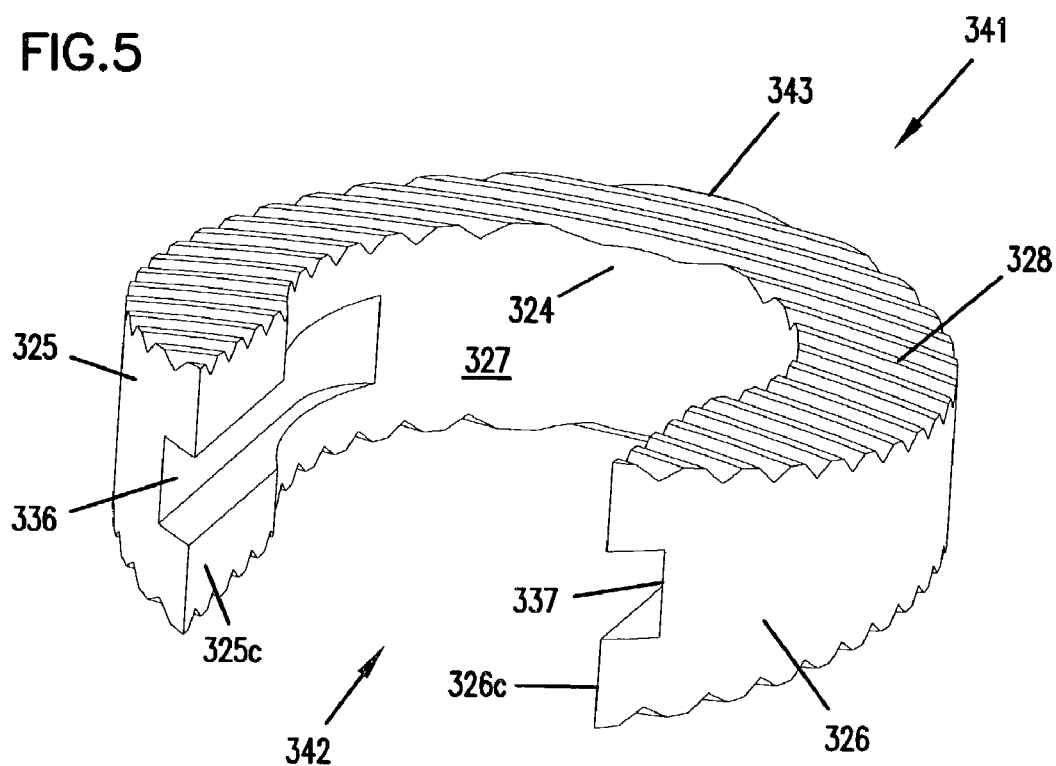
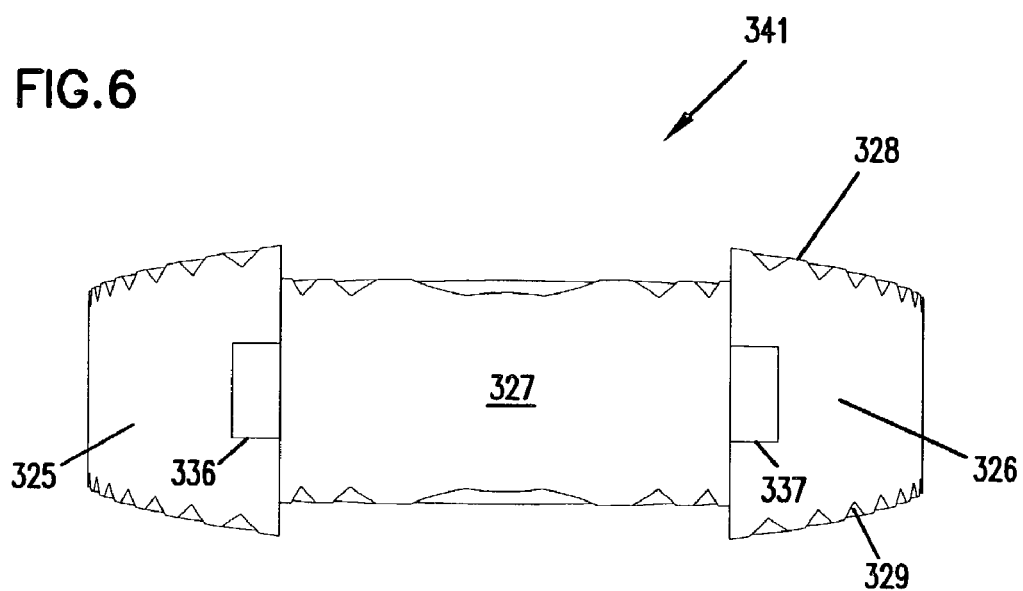

FIG.8A
FIG.8B
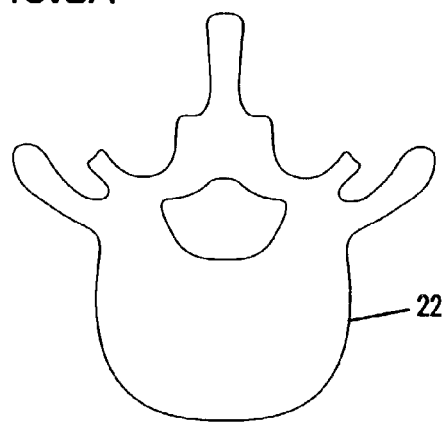
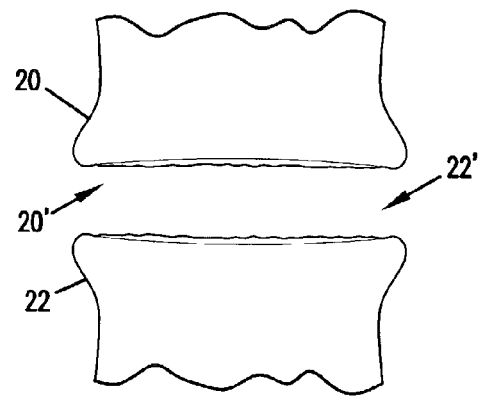
FIG.9A
FIG.9B
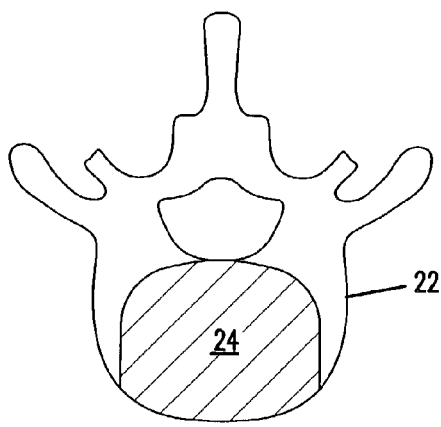
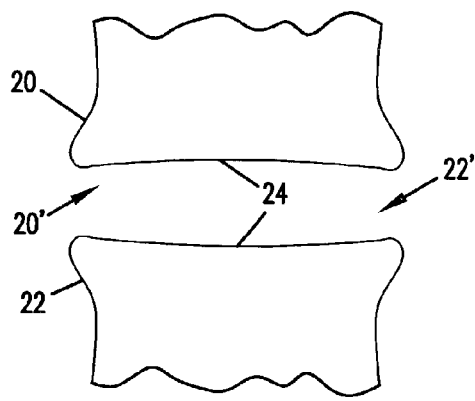
FIG.10A
FIG.10B
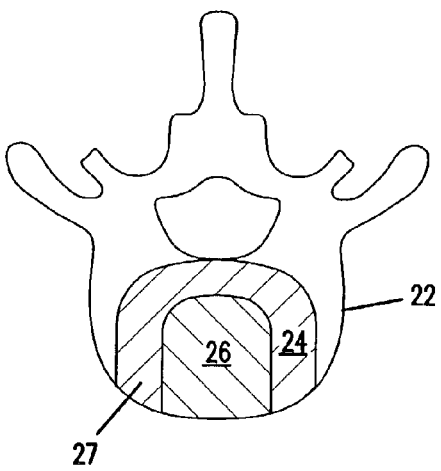
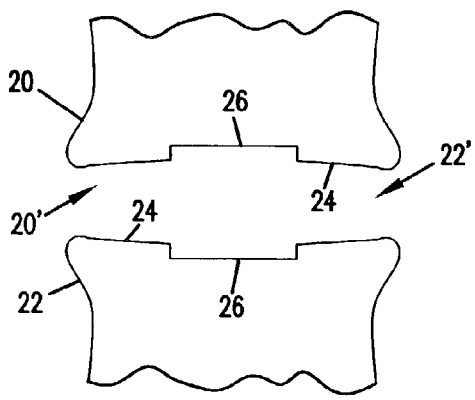

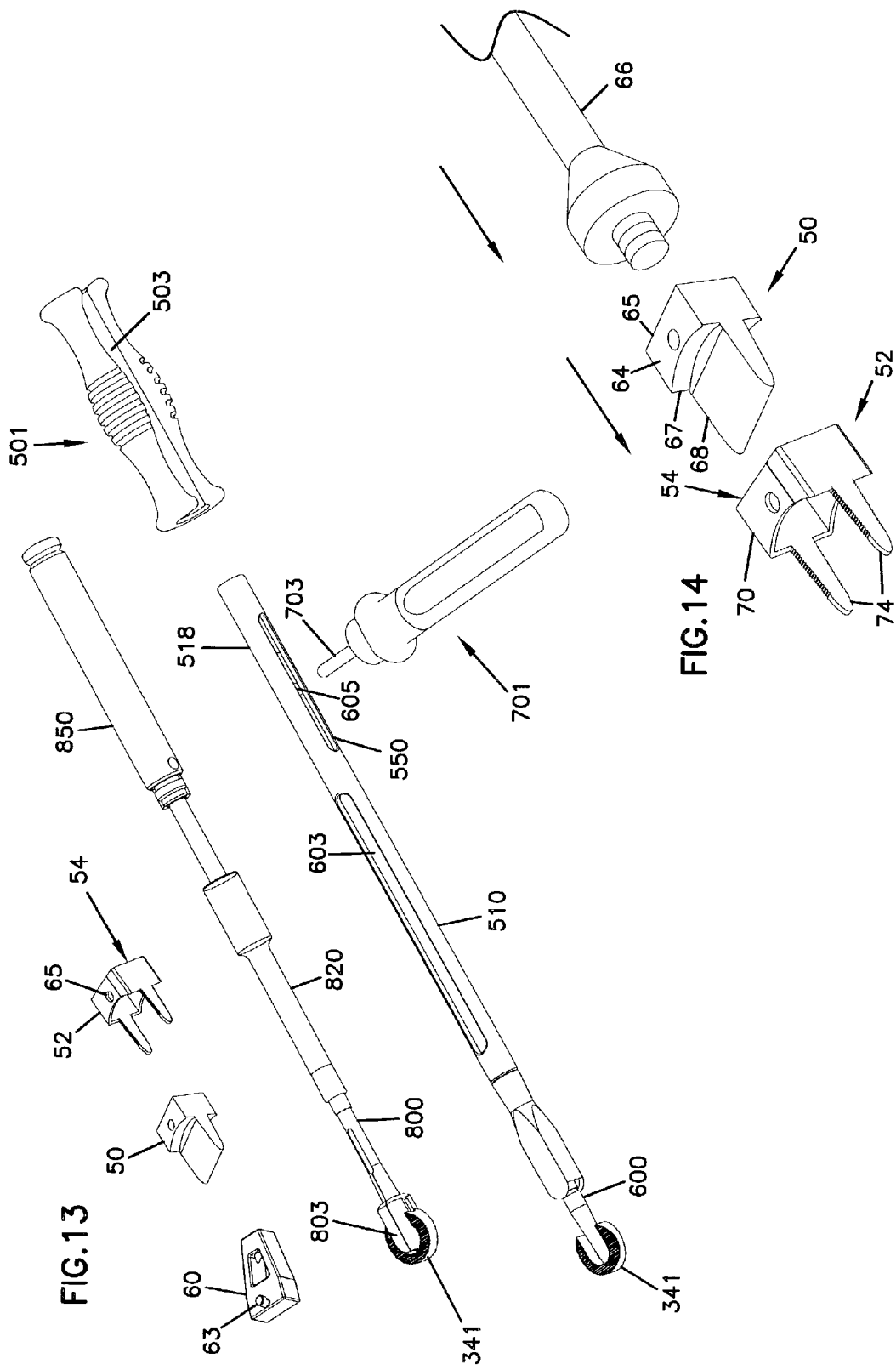

BONE IMPLANTS AND METHODS

CROSS-REFERENCE TO RELATED APPLICATIONS

This application claims the benefit of U.S. Patent Application 60/269,777, filed on Feb. 16, 2001, and is a continuation-in-part of U.S. patent application Ser. No. 09/896,926, filed on Jun. 28, 2001, now U.S. Pat. No. 6,635,060. U.S. patent application Ser. No. 09/896,926 is a continuation-in-part of U.S. patent application Ser. No. 09/611,237 filed Jul. 6, 2000, now U.S. Pat. No. 6,641,582.

FIELD OF THE INVENTION

This invention pertains to bone implants, instruments and procedures. Specifically, the invention provides bone implants, instruments and methods to facilitate fusion of bone. The invention is particularly suited for stabilization or fusion of the intervertebral disc space between adjacent vertebrae.

BACKGROUND OF THE INVENTION

Chronic back problems cause pain and disability for a large segment of the population. Frequently, the cause of back pain is traceable to diseased disc material between opposing vertebrae. When the disc material is diseased, the opposing vertebrae may be inadequately supported, resulting in persistent pain. Surgical techniques have been developed to remove all or part of the diseased disc material and fuse the joint between opposing vertebral bodies. Stabilization and/or arthrodesis of the intervertebral joint can reduce the pain associated with movement of a diseased intervertebral joint. Spinal fusion may be indicated to provide stabilization of the spinal column for a wide variety of spine disorders including, for example, structural deformity, traumatic instability, degenerative instability, post-resection iatrogenic instability, etc.

Generally, fusion techniques involve partial or complete removal of the diseased disc and packing the void area with a suitable matrix for facilitating a bony union between the opposing vertebral bodies.

Surgical devices for facilitating interbody fusion are known. Some devices are positioned external to the intervertebral joint during the fusion process. Other devices are positioned within the intervertebral joint. Devices positioned within the joint space typically distract the joint space and provide stabilization by causing tension on the annulus fibrosus and other supporting tissues surrounding the joint space. Examples of devices positioned within the joint space are disclosed in, for example, U.S. Pat. Nos. 5,458,638, 5,489,307, 5,055,104, 5,026,373, 5,015,247, 4,961,740, 4,743,256 and 4,501,269, the entire disclosures of which are incorporated herein by reference. Some systems use both external fixation and internal fixation devices.

Regardless of the type or location of the fusion device, a bone graft and/or other implant is often used to facilitate new bone growth. The surface area, configuration, orientation, surface texture and deformity characteristics of an implant or bone graft placed in the disc space can affect the stability of the joint during fusion and thus affect the overall success of a fusion procedure.

Accordingly, the present invention is directed to unique implants or bone grafts that can be inserted at a fusion site, with or without other stabilizing systems, and instruments and methods for inserting the same.

SUMMARY OF THE INVENTION

One inventive aspect of the present disclosure relates to an implant (e.g., a spinal implant) having a first component having support mechanical characteristics and a second component having mechanical characteristics for allowing bone in-growth. Other inventive aspects include systems and methods for implanting multi-component implants. It should be noted that the examples are provided for illustrative purposes and are not intended to limit the scope of the invention.

BRIEF DESCRIPTION OF THE DRAWINGS

FIG. 5 is a perspective view of a portion of the implant of FIG. 1;

FIG. 6 is a front elevational view of the implant of FIG. 5;

FIG. 8A is a top plan view of an inferior vertebrae prior to a preparation step according to the principles of the present invention;

FIG. 8B is a front elevational view of the inferior vertebrae of FIG. 8A and a corresponding superior vertebrae;

FIG. 9A is a top plan view of the inferior vertebrae of FIG. 8A after a preparation step according to the principles of the present invention;

FIG. 9B is a front elevational view of the inferior vertebrae and the superior vertebrae of FIG. 8B after the preparation step of FIG. 9A;

FIG. 10A is a top plan view of the inferior vertebrae of FIG. 9A after another preparation step according to the principles of the present invention;

FIG. 10B is a front elevational view of the inferior vertebrae and the superior vertebrae of FIG. 9B after the preparation step of FIG. 10A;

FIG. 13 is a perspective view of an implant kit that is an embodiment of the present invention;

FIG. 14 is a perspective view of a wedge and portal assembly of the implant kit of FIG. 13;

DETAILED DESCRIPTION OF THE INVENTION

Figure 1:
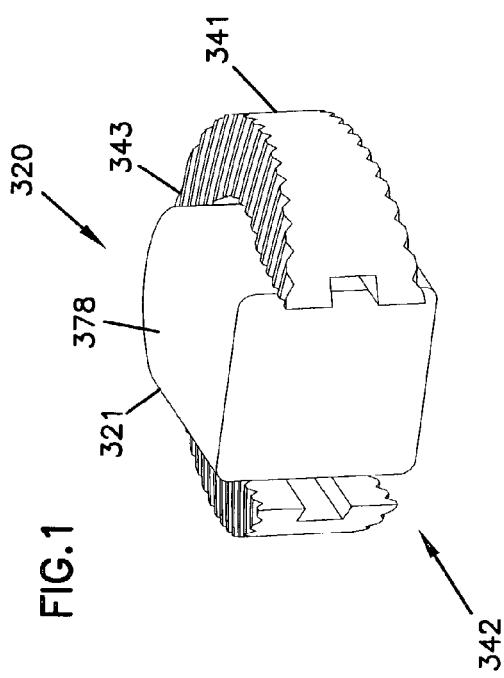
FIG. 1 is a perspective view of an implant that is an embodiment of the present invention.

The present invention is directed toward the fusion of bones. The invention provides natural and/or synthetic bone implants that can function as a bone graft between adjacent bones to be fused. The implants of the invention include unique arrangements, configurations and components to facilitate fusion and maintain stability during the fusion process.

The implants, instruments and methods of the invention can be used in a variety of bone fusion procedures. In some embodiments, the invention may be particularly advantageous for intervertebral stabilization or arthrodesis of the intervertebral disc space between adjacent vertebrae. Accordingly, for purposes of description herein, the invention will be described by reference to intervertebral fusion procedures in the lumbar region of the spine. However, this description is for exemplary purposes only and should not be construed to limit the intended scope of use of the disclosed implants, instruments or methods. For example, in the case of vertebral fusion, the implants, instruments and methods of the invention can be used to fuse cervical, thoracic, lumbar or lumbo-sacral vertebrae.

In general, the implants, instruments and methods of the invention are directed to facilitating greater continuity between the bone formed at the fusion site and the bones fused. The implants are also designed to provide greater structural support at the fusion site to maintain stability and alignment at the fusion site, to reduce healing time and optimize the structural integrity of the new bone formed at the fusion site. The implants of the invention can also facilitate the ease of implanting and positioning implants at a fusion site.

The implants can be prepared from natural materials, synthetic materials, or a combination of natural and synthetic materials. As used herein, "natural material" means "bone" and includes bone harvested from humans or animals. "Bone" may further include heterologous, homologous and autologous (i.e., xenograft, allograft, autograft) bone derived from, for example, fibula, tibia, radius, ulna, humerus, cranium, calcaneus, tarsus, carpus, vertebra, patella, ilium, etc. Bone may further include one or more bone products which have been partially or completely demineralized, prepared for transplantation (e.g., via removal of immunogenic proteins), and/or processed by other techniques. Additionally, the implants can be prepared from products made from bone, such as chips, putties, and other similar bone products. In some embodiments, human source bone is preferred for human applications. In a preferred embodiment, the bone of an implant can be cancellous and/or cortical.

Cortical implant material can be obtained from known long bones, such as the humerus, radius, ulna, tibia, femur, fibula, etc. Cancellous material can be obtained from the patella, distal condyles, tibial plateau, femoral head, etc. Cranial, pelvic (e.g. iliac crest) and patellar bone can advantageously provide both cortical and cancellous bone in a single piece. Indeed, these sources can provide an implant having cancellous bone surrounded on opposing sides by cortical bone.

"Synthetic materials" include non-bone materials such as titanium, stainless steel, porous titanium, ceramic, carbon fiber, silicon, methylmethacrylate, polytetrafluoroethylene, polycarbonate urethane, PEEK and other materials suitable for use as an orthopedic implant. Further, the materials may include any of the above synthetic materials combined with a natural bone material. For example, the material may comprise a combination of bioglass and bone chips or bone chips with a bonding agent. As stated above, an implant of the invention can consist solely of a synthetic material. In other applications, a synthetic material may be used in combination with cancellous bone.

In one embodiment, an implant can include a support component or member and a growth component or member. The support component includes a material having mechanical properties suitable for providing, support, stabilization or alignment at the fusion site. An exemplary material for the support component includes cortical bone. The growth component includes a material having mechanical or physical properties that allow or support new bone in-growth. An exemplary material for the growth component includes cancellous bone. In such an embodiment, the support component of the implant provides strength for column support and/or stabilization, and the growth component facilitates tissue growth, vascularization and deposition of new bone (e.g., by providing increased surface area). In one embodiment, the support component includes a material that provides greater axial column strength than the growth component, and the growth component includes a material that allows for enhanced bone in-growth as compared to the support component.

As indicated above, in some embodiments, the "support" portion (component) of an implant of the invention is provided by cortical bone or a natural or synthetic material having biomechanical and biological characteristics similar to cortical bone. The support portion provides support, stabilization, and facilitates alignment at the fusion site. The "growth" portion (component) of the implant can include a material that allows bone in-growth (i.e., an osteoconductive material) such as a bone growth matrix. In these embodiments, the growth portion provides a matrix or scaffold to support new bone growth. One preferred bone growth component that can also provide some support is cancellous bone. "Porous" synthetic materials can also act as a supporting, growth component. As used herein, a "porous synthetic material" includes, for example, porous titanium, porous ceramics, porous stainless steel and like materials. Such porous materials can provide characteristics of both the growth portion and the support portion of the implant.

In some embodiments, the growth component of the implant can be prepared from cancellous bone or alternatively a bone growth matrix shaped into any one of the advantageous configurations of growth components disclosed herein. Suitable bone growth matrices can be resorbable or nonresorbable, and with or without osteoinductive properties or materials. Examples of suitable osteoconductive matrices include synthetic materials, such as Healos™, available from Orquest, Mountain View, Calif. Examples of osteoinductive materials include bone marrow, blood platelets and/or bone morphogenic proteins (BMPs).

An implant of the invention can have one of several configurations including a single component or a plurality of components. In one embodiment, the implants have first and second bearing surfaces, which in use are positioned adjacent opposing vertebrae endplates. The bearing surfaces can include an engaging surface having a surface texture that enhances stability at the bone-implant interface and reduces the likelihood of motion during the fusion process. Examples of engaging surfaces suitable for the invention include ridges, knurls, grooves, teeth, serrations, etc.

Natural or synthetic bone implants of the invention can be manufactured using procedures known in the art. Methods for preparing natural bone implants are disclosed in for example, U.S. Pat. Nos. 6,033,438; 5,968,047; 5,585,116; 5,112,354; and 5,439,684; the entire disclosures of which are incorporated herein by reference.

DETAILED DESCRIPTION OF THE ILLUSTRATED EMBODIMENTS

The implants, instruments and methods of the invention will now be described by reference to the several drawing figures. The functional features of the implants of the invention can be embodied in any of a number of specific configurations. It will be appreciated, however, that the illustrated embodiments are provided for descriptive purposes and should not be used to limit the invention. In addition, in many exemplary embodiments, cortical and cancellous bone are used. It will be appreciated from an understanding of the present invention that the cortical or support and/or growth portions of the implants can be substituted with synthetic materials.

I. Representative Bone Implant

FIGS. 1–4 illustrate a multi-piece bone implant 320 that is a representative embodiment of the present invention. The bone implant 320 includes a bone support member 341 (also referred to as a support component or support portion) configured for intervertebral implantation. As best shown in FIG. 1, the bone support member 341 defines a cavity 327 (i.e., a void, pocket or channel) having an open end 342 positioned opposite from a closed end 343. The bone implant 320 also includes a growth member 321 (also referred to as a growth component or growth portion) having a shape that generally corresponds to or matches (i.e., complements) a shape of the cavity 327. The open ended configuration of the cavity 327 allows the growth member 321 to be inserted into the cavity 327 through the open end 342. In one embodiment, the growth member 321 is inserted after the bone support member 341 has been implanted between adjacent vertebrae. In another embodiment, the bone support member 341 is implanted such that the open end 342 of the bone support member 341 faces in an anterior direction (i.e., toward the ventral surface of the patient), and the growth member 321 is inserted into the cavity 327 using an anterior approach. Alternatively, the open end 342 may face in an anterior-lateral or lateral direction and the growth member 342 may be inserted using an anterior-lateral or lateral approach, respectively.

A. Bone Support Member

Figure 2:
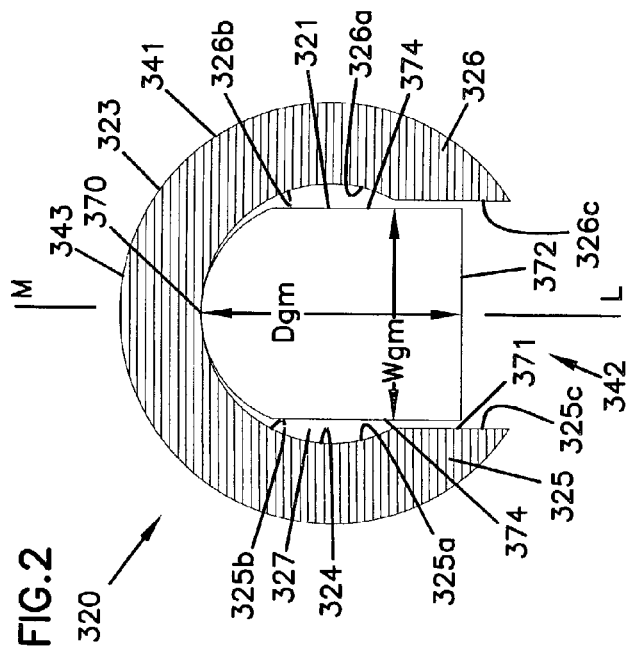
FIG. 2 is a top plan view of the implant of FIG. 1.

Referring to FIG. 2, the bone support member 341 of the implant 320 has a generally "C-shaped" configuration and includes outer and inner wall surfaces 323, 324. The shape of the bone support member 341 can also be described as "partial ring-shaped", "U-shaped", "semi-annular", or generally "horseshoe-shaped". In a preferred embodiment, the bone support member 341 includes first and second arms 325, 326 that are integrally connected at mid-line ML. Interior portions of the arms 325, 326 oppose one another so as to define the cavity 327 of the support member 341 therebetween. For example, the inner wall surface 324 includes opposing portions 325a and 326a, respectively, defined by the arms 325, 326. The opposing portions 325a, 326a extend on opposite sides of the mid-line ML from the open end 342 of the cavity 327 to the closed end 343 of the cavity 327.

Referring still to FIG. 2, the opposing portions 325a, 326a of the inner wall surface 324 include opposing curved portions 325b, 326b located adjacent the closed end 342 of the cavity 327 and opposing planar portions 325c, 326c located adjacent the open end 342 of the cavity 327. The curved portions 325b, 326b are shown having a concave, circular curvature. The planar portions 325c, 326c are generally parallel and define an insertion channel 371 for guiding the growth member 321 into the cavity 327 during insertion, and for aligning the growth member 321 within the cavity 327. In a preferred embodiment, the insertion channel is sufficiently wide between the planar portions 325c, 326c to receive the growth member 321 therein without requiring the arms 325, 326 to be flexed apart. The outer wall surface 323 of the support member 341 is shown including a convex, circular curvature that is concentric with the curvature defined by the curved portions 325b, 326b of the inner wall surface 324. In other embodiments, the support member 341 may be non-circular and/or not curved at all. For example, the support member 341 could include other shapes such as rectangles, squares, ovals, ellipses, etc.

Figure 23:
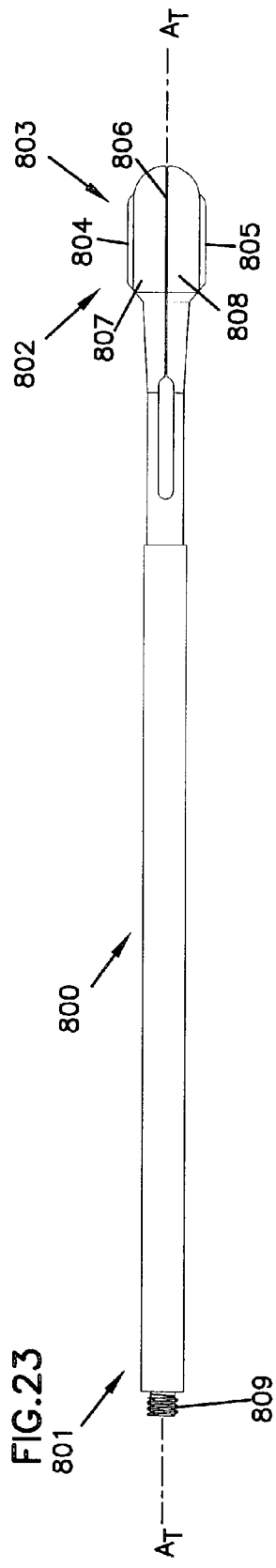
FIG. 23 is a top plan view of an implant insertion tool that is an embodiment of the present invention.
Figure 24:
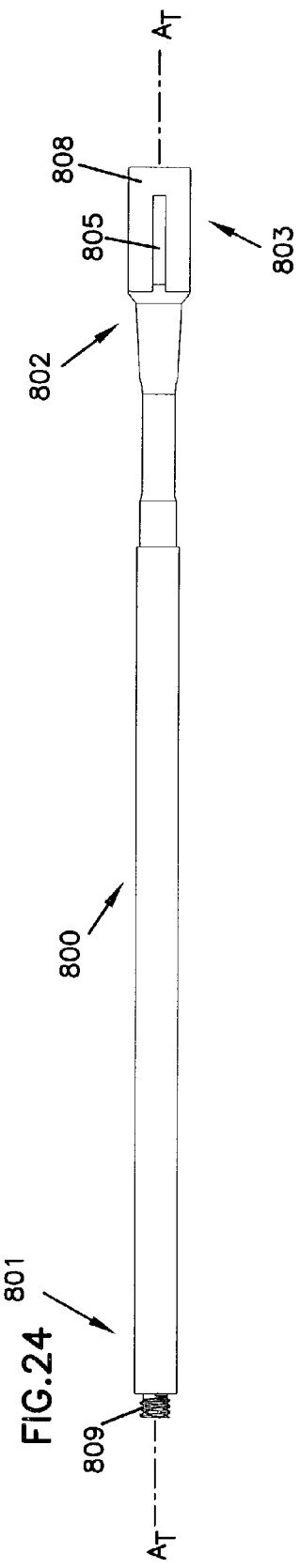
FIG. 24 is a side elevational view of the implant insertion tool of FIG. 23.

FIGS. 5 and 6 illustrate the support member 341 with the growth component 321 removed from the cavity 327. As can be seen, inner wall 324 includes a first groove 336 extending partially along first arm 325 and a second groove 337 extending partially along second arm 326. The grooves 336, 337 (e.g., slots) oppose one another and extend from the open end 342 of the cavity 327 toward the closed end 343 of the cavity 327. At least portions of the grooves 336, 337 are preferably defined by the planar portions 325c, 326c of the inner wall surface 324. Although grooves 336 and 337 are shown as being discontinuous, the groove can be continuous around inner wall 324. As will be described below, grooves 336 and 337 provide for attachment of a cover 350 (FIGS. 7A–7D) or an implant insertion tool 800 (FIGS. 23 and 24). While the grooves 336, 337 are shown including rectangular cross-sections, other shaped cross-sections such as rounded or triangular shapes could also be used. Further, the portions of the tool 800 or the cover 350 may or may not be complementary with the shapes of the grooves.

Figure 4:
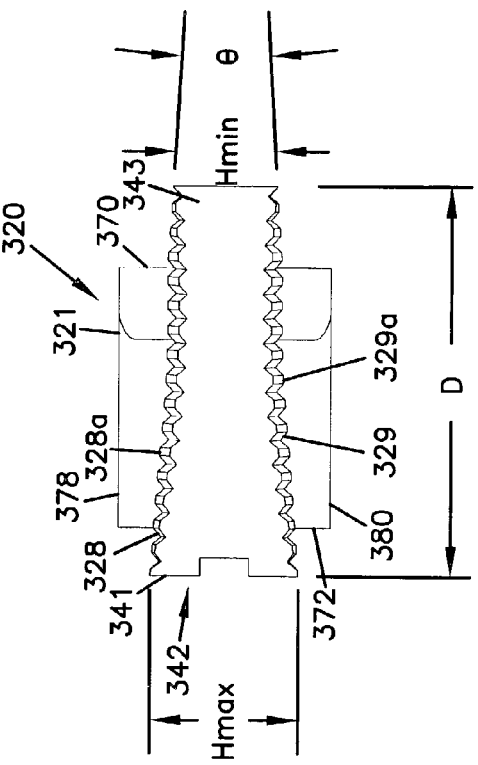
FIG. 4 is a side elevational view of the implant of FIG. 1.

Referring to FIG. 4, the bone support member 341 includes first and second bearing surfaces 328, 329 separated by a height or thickness of the support member 341. The inner and outer wall surfaces 323, 324 extend generally perpendicularly between the first and second bearing surfaces 328, 329. In the illustrated embodiment, the first bearing surface 328 includes an engaging surface comprising ridges 328a, and the second bearing surface 329 includes an engaging surface comprising ridges 329a. As discussed previously, engaging surfaces reduce the likelihood of post-implantation mobility of an implant.

Referring to FIGS. 5 and 6, the cavity 327 of the bone support member 341 preferably extends completely through the bone support member 341 between the top load bearing surface 328 and the bottom load bearing surface 329. Thus, the cavity 327 is open on the top and bottom sides of the bone support member 341 to facilitate exposure of top and bottom surfaces of the growth member 321 to the endplates of adjacent vertebrae when the growth member 321 positioned within the cavity 327.

While the bone support member 341 can have a constant height, in a preferred embodiment, the support member 12 is slightly tapered so as to define a wedge shape. In one embodiment, the bone support member 341 can include a lordotic taper at an angle θ in the range of 0–16 degrees (see FIG. 4). As shown in FIG. 4, in an exemplary embodiment with a lordotic taper, the support member 341 has a maximum thickness $H_{max}$ adjacent the open end 342 of the cavity 327 and a minimum thickness $H_{min}$ adjacent the closed end 343 of the cavity 327. In certain embodiments, a gradual taper is provided between the two thicknesses $H_{max}$ and $H_{min}$.

In one non-limiting embodiment, the support member 341 can have a maximum depth D in the range of 20–30 mm, a maximum width W in the range of 20–30 mm, an average thickness (the average of the two thicknesses $H_{max}$ and $H_{min}$) in the range of 6–24 mm. In another embodiment, the support member 341 is made of a homogeneous material having consistent (i.e., non-varying) mechanical properties. For example, in one embodiment, the support member 341 can include a bone material having a consistent degree of mineralization. In other embodiments, the support member 341 can include regions of decreased mineralization (e.g., demineralized portions) that provide regions of increased flexibility. In a preferred embodiment, the support member 341 includes a cortical bone cross-section from a femur or tibia bone.

B. Bone Growth Member

In certain embodiments, the growth member 321 preferably has a pre-manufactured or pre-formed shape. The terms "pre-manufactured" and "pre-formed" mean that the growth member 321 has a pre-defined shape prior to insertion in the cavity 327. In some embodiments, the pre-manufactured shape of the growth member 321 complements the shape of the cavity 327. In certain other embodiments, the growth member 321 includes multiple sub-units having pre-defined individual shapes and/or having collective shapes. In another embodiment, the growth member 321 includes a block of cancellous bone having a shape that complements the shape of the cavity 327.

As shown in FIG. 2, the bone growth member 321 includes a first end 370 positioned opposite from a second end 372. The first end 370 includes an end curvature that generally matches the curvature of the inner wall surface 324 adjacent the closed end 343 of the cavity 327. The bone growth member 321 also includes substantially parallel sidewall surfaces 374 that extend between the first and second ends 370 and 372. The second end 372 of the bone growth member 321 includes a substantially planar surface 376 that extends between the sidewall surfaces 374. In one preferred embodiment, the planar surface 376 is generally perpendicular relative to the sidewall surfaces 374. The bone growth member 321 also may include top and bottom surfaces 378 and 380 that are generally parallel relative to one another. In the embodiment shown, the top and bottom surfaces 378 and 380 extend between the first and second ends 370 and 372 of the bone growth member 321 and are generally perpendicular relative to the sidewall surfaces 374 and the planar end surface 376. In the depicted embodiment, the bone growth member 321 has a thickness $H_{gm}$ that is substantially constant from the first end 370 to the second end 372. In alternative embodiments, the thickness can taper gradually along the entire or part of the distance between the first and second ends 370 and 372. In some preferred embodiments, the thickness $H_{gm}$ of the bone growth member 321 is greater than the thickness $H_{max}$ of the bone support member 341. In these embodiments, the thickness $H_{gm}$ is preferably at least 2 or 3 mm greater than the thickness $H_{max}$.

In certain embodiments, the top and bottom surfaces 378 and 380 are adapted for direct contact with cancellous bone upon implantation. In these embodiments, to promote bone growth, it is desirable for the surface area provided by the top and bottom surfaces 378 and 380 to provide a significant portion of the total contact area provided by the implant 320 (the combined contact area provided by both the support member 341 and the bone growth member 321). In one embodiment, the top and bottom surfaces 378 and 380 provide at least 20 percent of the total contact area. In another embodiment, the top and bottom surfaces 378 and 380 provide at least 25 percent of the total contact area. In still another embodiment, the top and bottom surfaces 378 and 380 provide at least 30 or 40 percent of the total contact area. In a further embodiment, the top and bottom surfaces 378, 380 each have a width $W_{gm}$ (shown in FIG. 2) at least 40 percent as wide as the width W of the support member 341, and a depth $D_{gm}$ (shown in FIG. 2) at least 50 percent as deep as the depth D of the support member 341.

In a preferred embodiment, the bone growth member 321 has a non-threaded exterior. In this embodiment, the bone growth member 321 can be inserted into the cavity 327 by sliding the growth member 321 therein without requiring rotation. Additionally, the non-threaded configuration of the growth member 321 eliminates the need for tapping threads into the bone support member 341 or the opposing vertebral end plates between which the growth member 321 is desired to be implanted.

Figure 3:
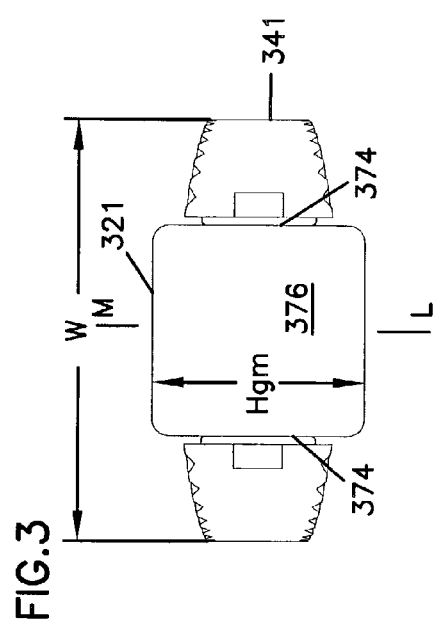
FIG. 3 is a front elevational view of the implant of FIG. 1.

Referring to FIG. 3, the bone implant 320 has a dome shape for limiting end plate removal and thereby minimizing subsidence. By "dome shape", it is meant that the implant is curved or tapered on the top and bottom surfaces 378 and 380 such that a thickness of the implant increases in a direction extending from the outer perimeter of the support member 341 toward the mid-line ML. In one embodiment, the degree of curvature of the dome is defined by a 3-inch radius.

Other implant configurations are disclosed in U.S. application Ser. Nos. 60/325,585 and 60/325,804 which are hereby incorporated by reference.

C. End Cap

Figure 7A:
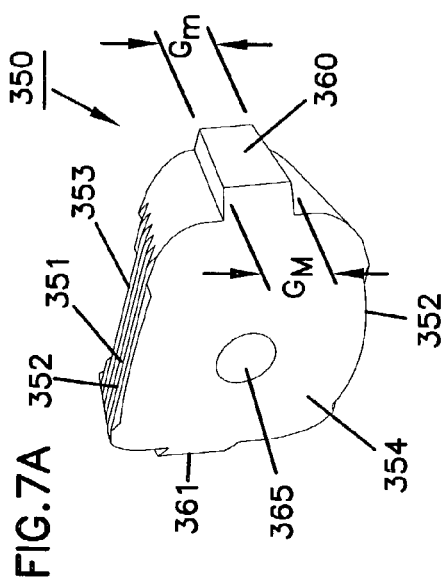
FIG. 7A is a perspective view of an implant cap that is an embodiment of the present invention.
Figure 7B:
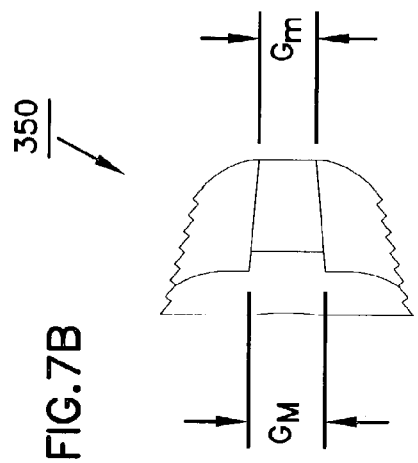
FIG. 7B is a side elevational view of the cap of FIG. 7A.
Figure 7C:
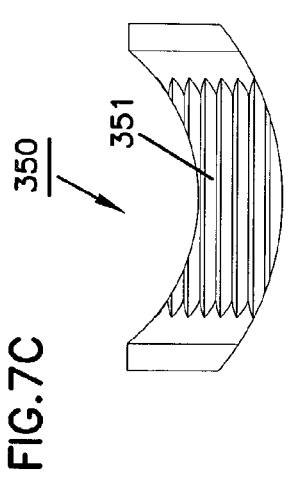
FIG. 7C is a top plan view of the cap of FIG. 7A.
Figure 7D:
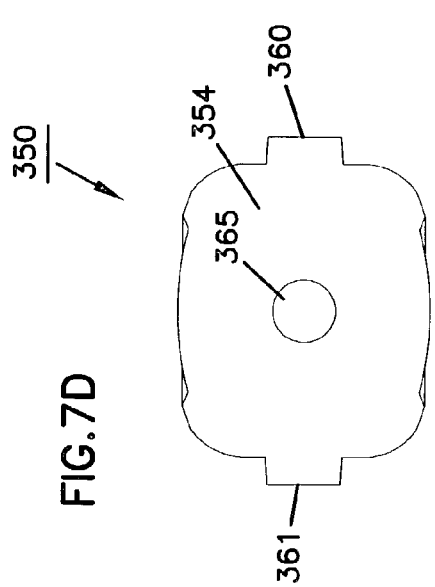
FIG. 7D is a front elevational view of the cap of FIG. 7A.

FIGS. 7A–7D illustrate an optional cap 350 for positioning in cavity 327 between arms 325 and 326. In the illustrated embodiment, cap 350 has a first bearing surface 351, a second bearing surface 352, an inner surface 353 and an outer surface 354. Bearing surface 351 includes an engaging surface 352 which can be similar to that of implant 320 (bearing surface 352 can also include an engaging surface). On each side, cap 350 includes a tab 360 and 361. Tabs 360 and 361 are configured to pass into grooves 337 and 336. As illustrated in FIGS. 7A and 7B, tab 360 (and 361) have a major height $G_M$, and minor height $G_m$. The difference in height $G_M$ and $G_m$ provides tabs 360 and 361 with a diverging taper from inner surface 353 to outer surface 354. Thus, when tabs 360 and 361 have passed into grooves 337 and 336 as cap 350 is advanced within arms 325, 326 the taper from height $G_m$ to height $G_m$ is selected to provide for a snug fit between tabs 360 and 361 and grooves 336 and 337 to retain cap 350 in position. That is, cap 350 is friction fit into implant 320. The grooves 336 and 337 of implant 320, and a cap, such as cap 350 can be used with other implants, such as implants 120 and 140.

Cap 350 can also include a bore 365 that may be threaded (not shown) which permits for attachment of an insertion tool having a threaded male end to mate with bore 365.

II. General Implantation Method

To implant the implant 320, a discectomy is performed on a patient to partially or completely remove a diseased disc between adjacent vertebrae 20, 22 (see FIGS. 8A and 8B). With the disc material removed, end plates 20', 22' of the adjacent vertebra 20, 22 are distracted/separated (e.g., with a wedge distractor). After the vertebra 20, 22 have been spaced-apart, first regions 24 (see FIGS. 9A and 9B) of the end plates 20', 22' are prepared/conditioned to receive the bone implant 10. For example, the end plates 20', 22' can be conditioned by rasping the end plates 20', 22' to remove cartilaginous material from the end plates 20', 22' and to smooth the cortical bone of the end plates 20', 22' by reducing surface irregularities. Next, second regions 26 of the end plates 20', 22' are prepared within the first regions 24 (see FIGS. 10A and 10B). In a preferred embodiment, the second regions 26 have smaller areas than the first regions 24 and are subsets or sub regions of the first regions 24. In one embodiment, the second regions 26 are prepared by using a cutting tool (e.g., a chisel) to remove the cortical bone from the second regions 26 and expose underlying cancellous bone. In this embodiment, the exposed cancellous bone at the second regions 26 is preferably surrounded by partial rings 27 of cortical bone (e.g., including the epiphyseal ring).

Figure 11:
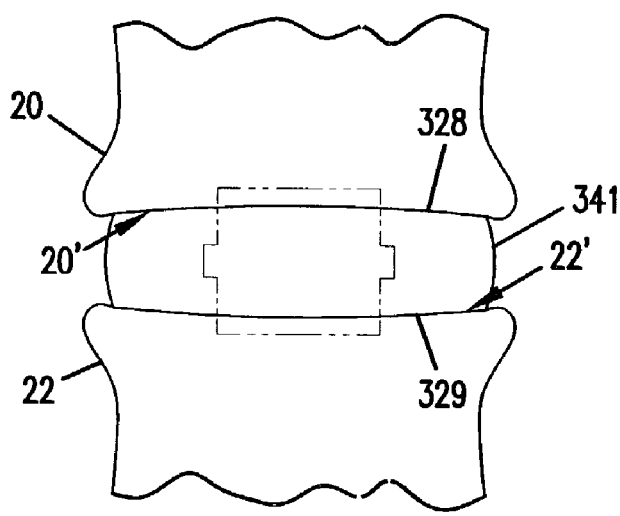
FIG. 11 is a front elevational view of the inferior vertebrae and the superior vertebrae of FIG. 10B after placement of a support member in accordance with the present invention.
Figure 12:
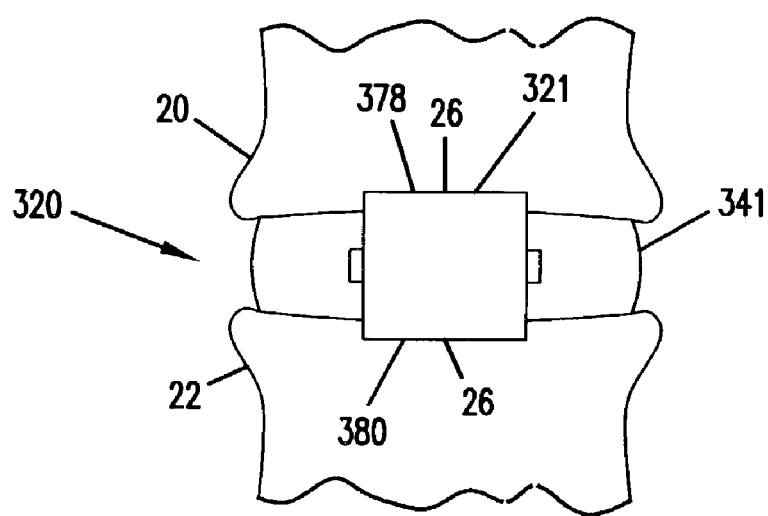
FIG. 12 is a front elevation view of the inferior vertebrae and the superior vertebrae of FIG. 11 after placement of a growth member in accordance with the present invention.

After preparation of the end plates 20', 22', the bone support member 341 is inserted between the distracted vertebrae 20, 22 (see FIG. 11). As so inserted, the top and bottom load bearing surfaces 328, 329 of the support member 341 directly engage the partial rings 27 of cortical bone to provide column support. After implantation of the support member 341, the bone growth member 321 is inserted into the cavity 327 through the open end 342. As so inserted, the top and bottom sides 378 and 380 of the growth member 341 directly contact the exposed cancellous bone of the second regions 26 to provide a fusion lattice (see FIG. 12).

In a preferred embodiment, each first region 24 is coextensive with a majority of the surface area of each end plate 20', 22'. As shown in FIGS. 9A and 9B, each first region 24 covers substantially all of the surface area of each corresponding end plate 20', 22'. Thus, in such an embodiment, the implant 320 is sized to fill a majority of the intervertebral space between the end plates 20', 22' and to contact a majority of the surface area of each end plate 20', 22'. In one embodiment, each second region 26 defines an area that coincides with 20–80 percent of the total area defined by each corresponding first region 24. In another embodiment, each second region 26 defines an area that coincides with 30–70 percent of the total area defined by each corresponding first region 24. In yet another embodiment, each second region 26 defines an area that coincide, with 40–60 percent of the total area defined by each corresponding first region 24.

III. Implantation Kit

FIG. 13 illustrates an embodiment of a kit (i.e., an instrument set) for implanting the bone implant 320 of FIG. 1. The kit includes a wedge distractor 50 for providing a desired spacing between two vertebrae desired to be stabilized. The kit also includes a portal 52 for maintaining the spacing between the vertebrae after the wedge distractor 50 has been removed from between the vertebrae. The portal 52 includes a window 54 for allowing access to the space between the distracted vertebrae. Certain embodiments of the wedge distractor and portal system have previously been disclosed in U.S. Pat. No. 6,224,599, incorporated herein by reference. The kit further includes instruments that can be inserted through the window 54 of the portal 52 for preparing the vertebral end plates. For example, the kit includes a rasp 600 for removing cartilage from the vertebral end plates and for conditioning the cortical bone of the vertebral end plates. A box chisel 510 is included in the kit for removing cortical bone from the vertebral end plates to provide regions of exposed cancellous bone.

The box chisel 510 includes a hollow handle 518 configured to slide over a shaft 603 of the rasp 600 such that the shaft 603 functions as a guide for controlling the cutting location of the chisel 510. A side handle 701 having an alignment pin 703 is adapted to maintain rotational alignment between the rasp 600 and the box chisel 510. The alignment pin 703 inserts within an opening 605 defined by the shaft 603 of the rasp 600 and also extends through a slot 550 defined by the handle 518 of the chisel 510. The slot 550 allows the chisel 510 to be moved axially back and forth along the rasp handle to provide a chiseling motion. As the chisel 510 is moved along the rasp handle, the pin 703 slides along the slot 550. The range of axial motion of the chisel 510 is limited by the length of the slot 550. During chiseling, the side handle 701 is preferably grasped to stabilize the rasp 600. A slap hammer 501 can be used to provide greater impact forces for cutting the vertebrae with the chisel 510. The slap hammer 501 includes a slot 503 for allowing the slap hammer 501 to be moved past the alignment pin 703 when slid over the handle 518 of the chisel 510.

The kit further includes an insertion tool 800 having an insertion head 803 (also referred to as a "working end") sized to fit within the cavity 327 of the bone support member 341. In use, the bone support member 341 is mounted on the insertion head 803, and the insertion tool 800 is used to insert the bone support member 341 between the distracted and pre-conditioned vertebrae. Thereafter, the insertion head 803 is removed from the cavity 327 of the bone support member 341, and the growth member 321 is inserted into the cavity 327 through the open end 342 of the cavity 327. Alternatively, a conventional tool, such as a forceps, can be used to insert the growth member 321 into the cavity 327. After the implant 320 has been implanted into the intervertebral space, a portal extractor 60 can be used to remove the portal 52.

A. Wedge Distractor, Portal and Portal Extractor

FIG. 14 shows the wedge distractor 50 and the portal 52 of the kit of FIG. 13 in alignment with one another. The wedge distractor 50 includes a generally rectangular base portion 64. A back side 65 of the base portion 64 defines a threaded opening (not shown) sized to receive a threaded end of a handle 66. A vertebral wedge 68 projects forwardly from a front side 67 of the base portion 64.

The portal 52 includes a generally rectangular frame 70 defining the portal window 54. The portal window 54 is sized to receive the wedge distractor 50 with a friction fit between the base portion 64 of the wedge distractor 50 and the frame 70 of the portal 52. The portal 52 also includes spaced apart distraction paddles 74 that align on opposite sides of the vertebral wedge 68 when the wedge distractor 50 is press fit within the portal 52. The distraction paddles 74 and the vertebral wedge 68 preferably have substantially the same side profile.

Referring to FIG. 13, the portal extractor 60 is sized to fit within window 54 of portal 52. Handle 66 (shown in FIG. 14) preferably connects to extractor 60. Tab 63 of extractor 60 fits within opening 65 of portal 52 to allow portal 52 to be pulled from the intervertebral space.

B. Rasp

Figures 15, 16:
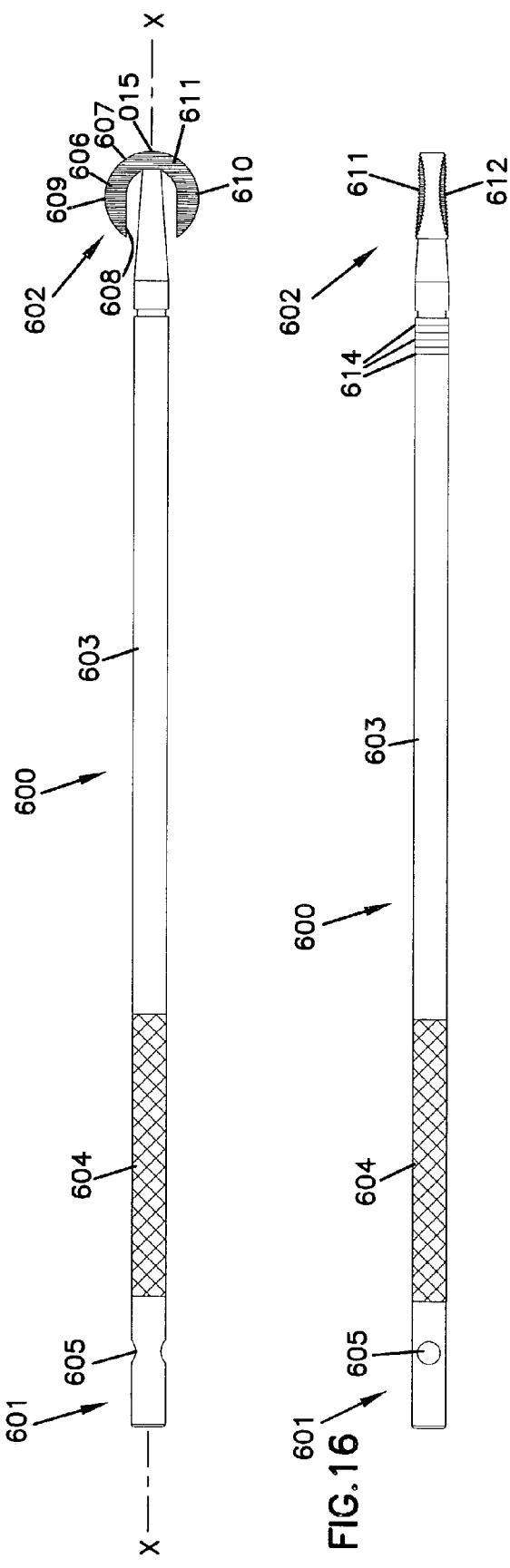
FIG. 15 is a top plan view of a rasp that is an embodiment of the present invention.
FIG. 16 is a side elevational view of the rasp of FIG. 15.

FIG. 15 is a top view and FIG. 16 a side view of the rasp 600 of the kit of FIG. 13. The rasp 600 is adapted to function as both as a trial sizer, i.e. for a particularly sized and shaped implant, and a rasp. Rasp 600 has a proximal end 601 and a distal end 602 spaced along longitudinal axis X—X. At the proximal end 601 of shaft 603, there is a roughened area 604 that can be in the form of knurls, etchings, grooves, ridges, or other suitable patterns to enhance manual gripping of the shaft 603. The opening 605 for receiving the alignment pin 703 of handle 701 extends transversely through the proximal end 601 of the shaft 603. As previously indicated, the opening 605 and alignment pin 703 assist in maintaining rotational alignment between the rasp 600 and the chisel 510.

Figure 19:
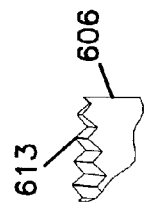
FIG. 19 is an enlarged partial top plan view of a rasp head of the rasp of FIG. 15.
Figure 18:
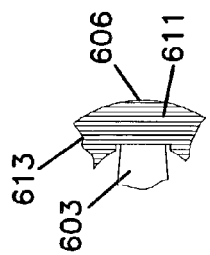
FIG. 18 is an enlarged partial perspective view of teeth on a rasp head of FIG. 15.

At the distal end 602, rasp 600 includes a rasp head 606. In the illustrated embodiment, rasp head 606 includes an outer wall 607, an inner wall 608 and has a generally "C-shaped" configuration with a first arm 609 continuous with a second arm 610. The inner wall 608 defines a pocket or receptacle which is sized to complement and receive the distal end of the chisel 510. The first arm 609 and second arm 610 are spaced apart from the shaft 603. Rasp head 606 includes a first engaging surface 611 and a second engaging surface 612. In the illustrated embodiment, the first and second engaging surfaces 611, 612 have ridges 613 (see FIGS. 17–19). In alternative embodiments, knurls, etchings, teeth, grooves or other suitable patterns may be substituted for ridges 613.

Figure 17:
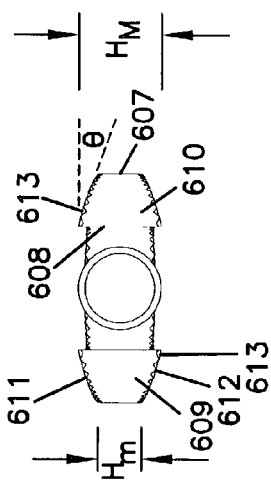
FIG. 17 is a proximal end-on elevational view of the rasp of FIG. 15.

As illustrated best in FIG. 17, in this embodiment, rasp head 606 has a major height $H_M$ and minor height $H_m$. The taper from the major height to the minor height can be from about 0° to about 16°. The shape and configuration of the rasp head 606 corresponds to the shape and configuration of an implant. In one embodiment, the rasp head 606 corresponds in size and configuration with the support component 341 of the two-part implant 320 of FIGS. 1–4. In such an embodiment, the rasp head 606 preferably has the same lordotic taper angle and the same dome curvature as the support member desired to be implanted. The space between the first and second arms 609, 610 of the rasp head 606 corresponds generally with the shape of the growth component 321 of the implant 320. It will be appreciated, however, that the configuration of the rasp head 606 can be square, rectangular, circular, oval, etc., depending on the configuration of the implant(s) to be inserted into the channel.

As a trial sizer, the rasp 600 provides a means for determining the appropriate size bone cutting instrument and implant to use for a particular implant site. Multiple rasps 600 are provided, with incrementally different sized, shaped, and/or tapered rasp heads 606 corresponding to different sized, shaped, and/or tapered implants. The surgeon inserts and removes the various rasps 600 and determines (e.g., via evaluation of the frictional fit) which one is the correct size for the intervertebral space. The ridges 613 on the upper and lower surfaces of the rasp head act as a rasp to condition the end plates of the upper and lower adjacent vertebrae.

Proximal to the distal end 602, the shaft 603 of the rasp 600 also includes markings 614 at predetermined distances from the distal edge 615 of the rasp head. During use, markings 614 provide the surgeon with an indication of the depth of distal penetration of rasp 600 between adjacent vertebrae.

C. Box Chisel

Figure 20:
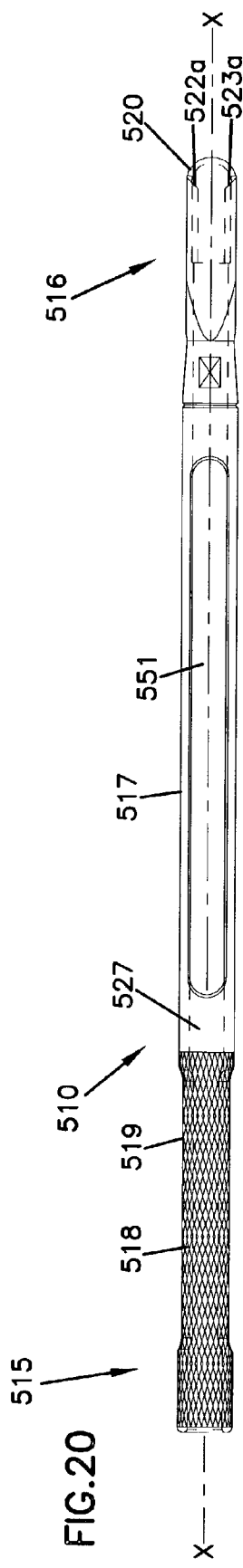
FIG. 20 is a top plan view of a bone-cutting instrument that is an embodiment of the present invention.
Figure 21:
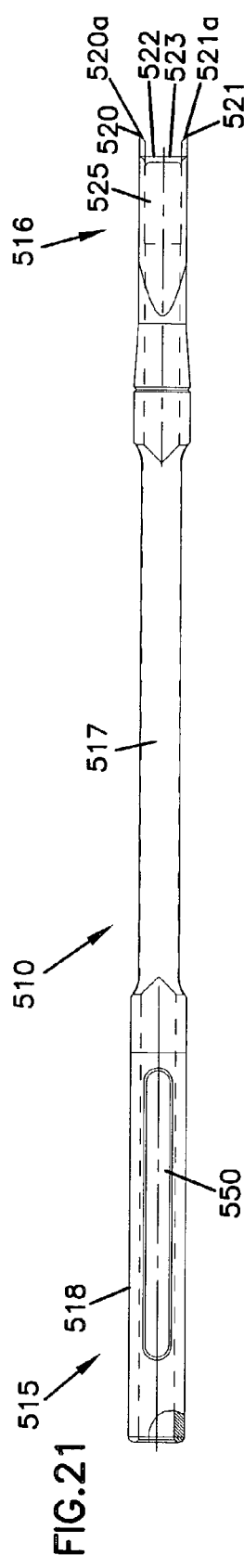
FIG. 21 is a side elevational view of the bone-cutting instrument of FIG. 20.

FIG. 20 is a top view and FIG. 21 a side view of the chisel 510 shown in the kit of FIG. 13. Chisel 510 has a proximal end 515 and a distal end 516 spaced along longitudinal axis X—X. At the proximal end 515 of shaft 517 there is a handle 518 for operating chisel 510. The handle 518 has a roughened area 519 that can be in the form of knurls, etchings, grooves, ridges, or other suitable patterns to enhance manual gripping of the handle 518. At the distal end 516, chisel 510 includes a first cutting edge 520, a second cutting edge 521, and third and fourth cutting edges 522 and 523. In the illustrated embodiment, cutting edges 520, 521, 522 and 523 are at the distal end of chamber 525. First, second, third, and fourth cutting edges 520, 521, 522 and 523 are beveled 520a, 521a, 522a, and 523a, respectively, to facilitate cutting and removal of bone. An internal hollow bore 527 extends from the proximal end 515 through the chisel 510 to the distal end 516 to receive the shaft 603 of rasp 600 and to receive bone.

In the illustrated embodiment, elongated openings 550 and 551 extend through the handle 518 and shaft 517, respectively, of the chisel 510. As described previously, opening 550 allows for alignment of the chisel 510 with rasp 600. Opening 551 provides additional access to the internal bore 527 for cleaning the instrument and reduces the weight of the instrument.

Figure 22:
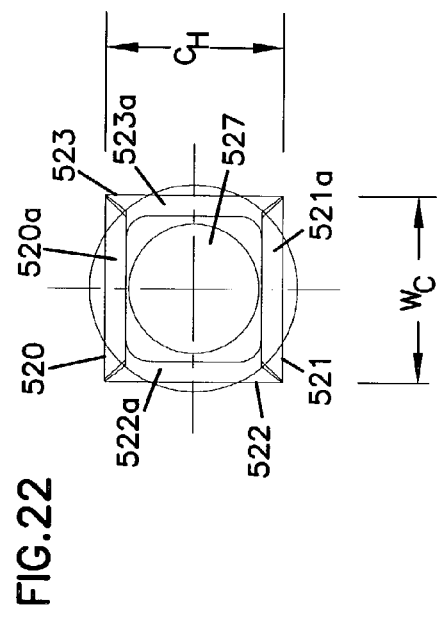
FIG. 22 is a distal end-on elevational view of the bone-cutting instrument of FIG. 20.

FIG. 22 is a distal end-on view of chisel 510 showing that first and second cutting edges 520 and 521 define a height dimension $C_H$ and the cutting edges 522 and 523 define a width dimension $W_C$. The perimeter configuration of cutting edges 520, 521, 522, and 523 in FIG. 22 is a rectangular shape particularly suited for preparing a channel or implant bore between adjacent bones for insertion of a two-part implant having a configuration such as that of the implant 320 shown in FIG. 1.

As previously indicated, implant 320 includes growth member 321, such as cancellous bone, and support member 341, such as cortical bone. The growth member 321 has a similar size and shape as the distal end of the chisel 510

(e.g., dimension $W_{gm}$ of growth member 321 corresponds to dimension $W_C$ of chisel 510 and dimension $H_{gm}$ of growth member 321 corresponds to dimension $C_H$ of chisel 510). Also, the end curvature (i.e., at end 370) of the growth member 321 corresponds to the curvature of edges 520 and 521 of the chisel 510. The support member 341 has a similar size and configuration as the rasp head (see for example FIGS. 15, 16). The support member 341 of the implant may be the same size as the rasp head, or it can be larger or smaller than the rasp head. The support member 341 of the implant can be about 0 mm to about 4 mm larger in height than the rasp head. The height dimension $C_H$ of the chisel 510 can be about 3 mm taller than the maximum height of the support member 321 of the implant. It will be appreciated, however, that the perimeter configuration of cutting edges 520, 521, 522, and 523 can be square, circular, oval, etc., depending on the external configuration of the implant to be inserted into the channel. The length of the first and second cutting edges 520 and 521 can vary to correspond with the depth of the vertebrae.

To cut different sized channels, a set of chisels 510 will be available which has instruments with incrementally different sizes of cutting edges 520, 521, 522, 523 corresponding to a particular size implant. For example, chisels 510 having first and second cutting edges 520, 521 with different heights $C_H$ will be available to permit the surgeon to select a cutting edge height corresponding to a particular disc space height. In addition, it will be appreciated that the illustrated cutting edges 520 and 521 (and 522 and 523) are parallel. In alternative embodiments, cutting edges 520 and 521 (and 522 and 523) can form a converging or diverging taper.

D. Insertion Tool

Figure 25:
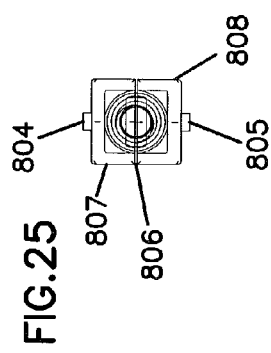
FIG. 25 is a distal end-on elevational view of the implant insertion tool of FIG. 23.

FIGS. 23–25 illustrate the insertion tool 800 of the kit of FIG. 13. As illustrated, implant insertion tool 800 has a proximal end 801 and a distal end 802 having a working end 803. Working end 803 includes tabs 804 and 805 that fit cooperatively within grooves 336, 337 of the support member 341 of the implant 320. In addition, the working end 803 includes a slot 806 that permits resilient/elastic arms 807 and 808 to flex or expand laterally away from axis $A_T$.

Figure 26:
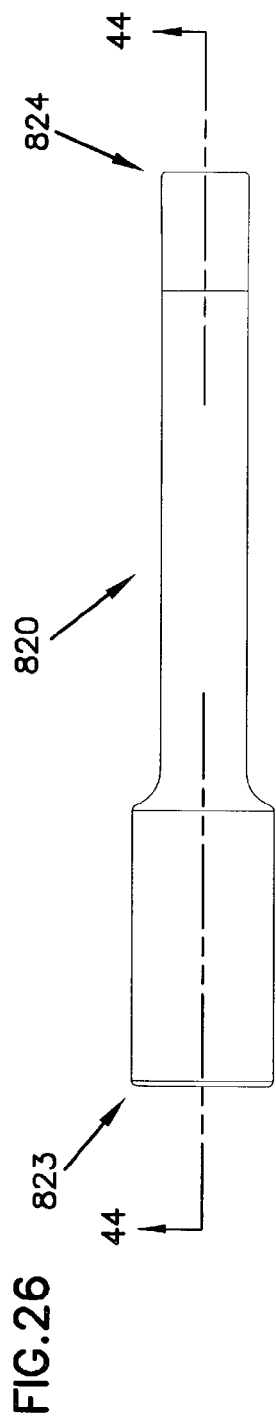
FIG. 26 is a side elevational view of a sleeve that is an embodiment of the present invention.
Figure 27:
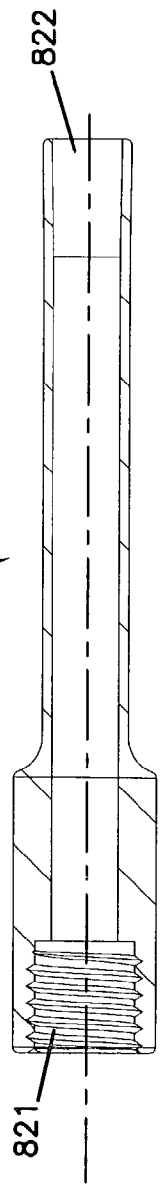
FIG. 27 is a cross-sectional view of the sleeve of FIG. 26.
Figure 28:
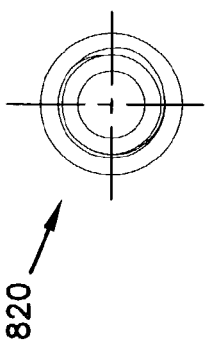
FIG. 28 is an end-on elevational view of the sleeve of FIG. 26.

In a typical embodiment, arms 807 and 808 are spring biased to expand away (e.g., laterally) from axis $A_T$ in the normal, relaxed position. A sleeve 820 (FIGS. 26–28) can then be slid from the proximal end 801 of the insertion tool 800, over the slot 806, to force arms 807 and 808 towards (e.g. medially) axis $A_T$. That is, when the sleeve is advanced distally it brings arms 807 and 808 together towards axis $A_T$. In this position, the working end 803 of implant insertion tool 800 can be inserted into an implant. Similarly, where useful for additional control, tabs 804 and 805 can be inserted into grooves 336, 337 of an implant. The sleeve can then be slid towards the proximal end to allow arms 807 and 808 to expand away from axis $A_T$ to provide friction holding of an implant on the working end 803. After placement of an implant, the sleeve can be slid distally to bring arms 807 and 808 back toward axis $A_T$ to remove implant insertion tool 800, leaving the implant in place. Other arrangements providing for expansion and contraction of arms 807, 808, relative to axis $A_T$ also are contemplated by this disclosure.

Thus, an implant can be mounted on the working end 803 of implant insertion tool 800 allowing the surgeon to manipulate an implant via tool 800 into a suitable position at the fusion site.

Figure 31:
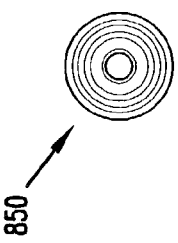
FIG. 31 is an end-on elevational view of the handle of FIG. 29.
Figure 29:
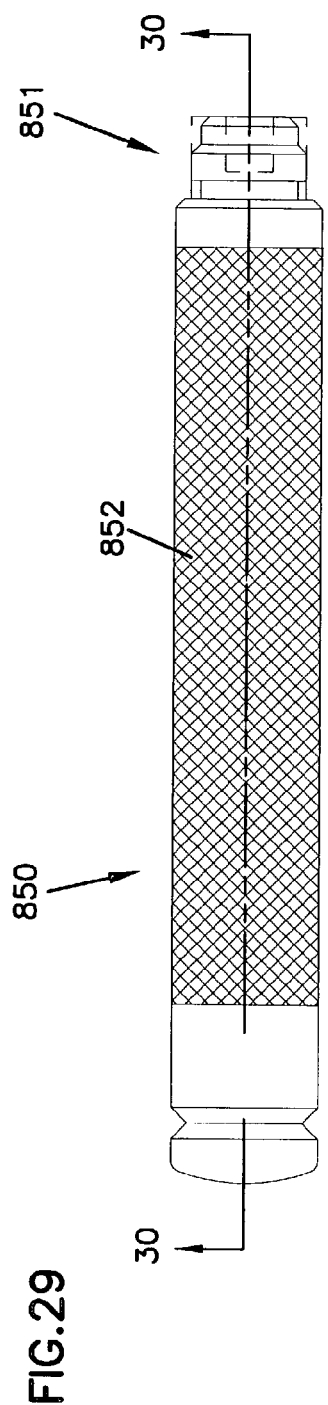
FIG. 29 is a top plan view of an insertion tool handle that is an embodiment of the present invention.
Figure 30:
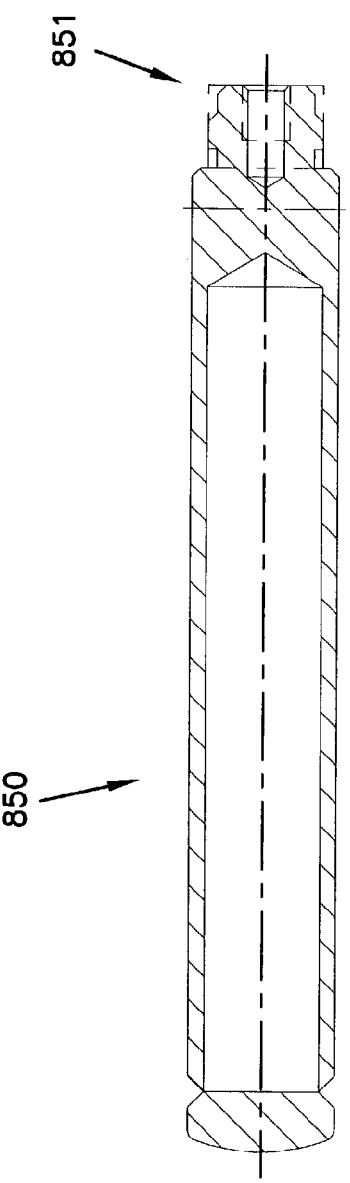
FIG. 30 is a cross-sectional view of the handle of FIG. 29 taken along line 30—30.

Referring back to FIGS. 23 and 24, in one embodiment the insertion tool 800 has a threaded region 809 at the proximal end 801. The threaded region 809 threads within a distal end 851 of a handle 850 (shown in FIGS. 29–31). The handle 850 has a roughened area 852 that can be in the form of knurls, etchings, grooves, ridges, or other suitable patterns to enhance manual gripping of the handle 850. In one embodiment, the distal end 851 of the handle 850 has exterior threading to match internal threading 821 on a sleeve 820. The sleeve 820 is hollow and has a bore 822 extending from the proximal end 823 to the distal end 824, and which is sized to fit over the proximal end 801 of the implant insertion tool 800. When the sleeve 820 is not being used to force the arms 807, 808 of the insertion tool toward one another, the internal threadings 821 can be threaded on the distal end 851 of the handle 850 to prevent unintended sliding of the sleeve 820.

Figure 32:
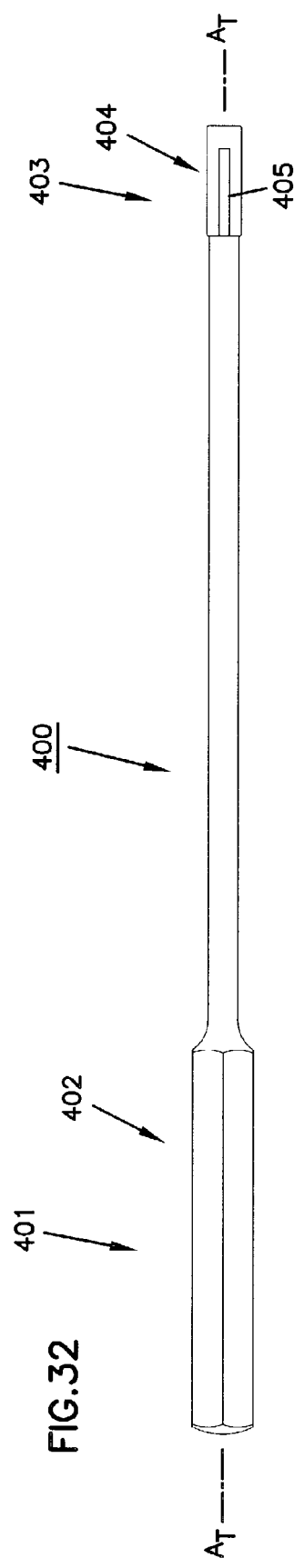
FIG. 32 is side elevational view of an implant insertion tool that is another embodiment of the present invention.
Figure 33:
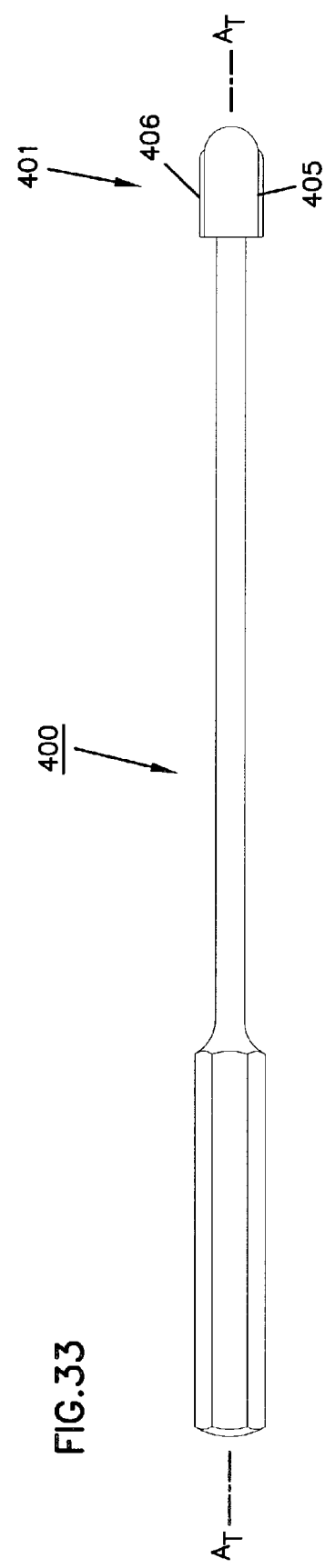
FIG. 33 is a top plan view of the implant insertion tool of FIG. 32.

FIGS. 32 and 33 illustrate an alternative embodiment of an implant insertion tool 400 suitable for use with an implant of the invention. As illustrated, implant insertion tool 400 has a proximal end 401 including a handle 402 for operating the instrument and a distal end 403 having a working end 404. Working end 404 include tabs 405 and 406 that fit cooperatively within grooves 336 and 337 of implant 320. Thus, implant 320 can be mounted at the working end 404 of implant insertion tool 400 allowing the surgeon to manipulate implant 320 via tool 400 into a suitable position at the fusion site.

IV. Method of Implantation Using Kit

In one embodiment, a technique for practicing the method of FIGS. 8–12 involves using the kit of FIG. 13. In practicing the method, a window, approximately the width of the portal 52 is cut, symmetrically about the midline, in the annulus and a complete discectomy is performed. Preferably, the lateral annulus is retained to act as a tension band around the implant 320.

After cutting the window in the annulus, the appropriate sized wedge distractor 50 and portal 52 are selected based on pre-operative templating. A sizing chart for various components of the kit is set forth below. The dimensions listed correspond to the heights of portions of the components that are inserted into the intervertebral space.

| INSTRUMENT LETTER CODE | A | B | C | D | E |
|---|---|---|---|---|---|
| PORTAL | 10 mm | 12 mm | 14 mm | 16 mm | 18 mm |
| DISTRACTOR WEDGE | 10 mm | 12 mm | 14 mm | 16 mm | 18 mm |
| RASP/TRIAL | 10 mm | 12 mm | 14 mm | 16 mm | 18 mm |
| CORTICAL GRAFT | 10 mm | 12 mm | 14 mm | 16 mm | 18 mm |
| BOX CHISEL | 13 mm | 15 mm | 17 mm | 19 mm | 21 mm |
| INSERTER HEAD | 13 mm | 15 mm | 17 mm | 19 mm | 21 mm |
| CANCELLOUS BLOCK | 13 mm | 15 mm | 17 mm | 19 mm | 21 mm |

Figure 34:
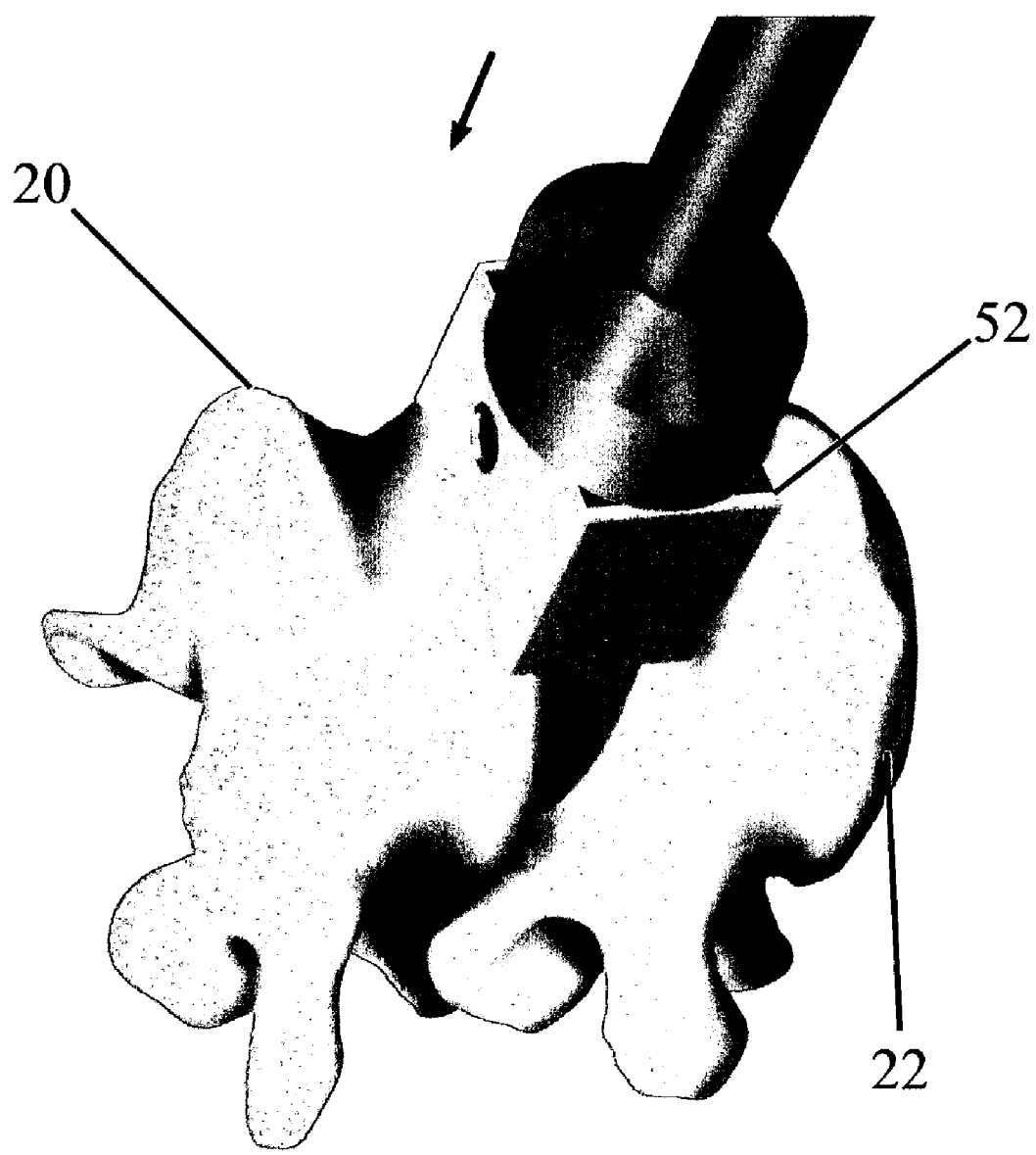
FIG. 34 is a perspective view of a portal insertion step according to the principles of the present invention.

Once the wedge distractor 50 and portal 52 of the appropriate size have been selected, the portal 52 is inserted over the wedge distractor 50, and the combined unit is then delivered into the midline of the disc space until a desired spacing and annular tension is achieved between the adjacent vertebrae 20, 22. Proper placement is achieved when the portal 52 is flush with the vertebrae 20, 22 as shown in FIG. 34. The proper position of the portal 52 can be confirmed by utilizing fluoroscopy.

With the portal in the position shown in FIG. 34, the slap hammer 501 can be used to help facilitate the removal of the wedge distractor 50 from the portal 52. Additional discectomy or posterior decompression can be completed, if necessary.

Figure 35:
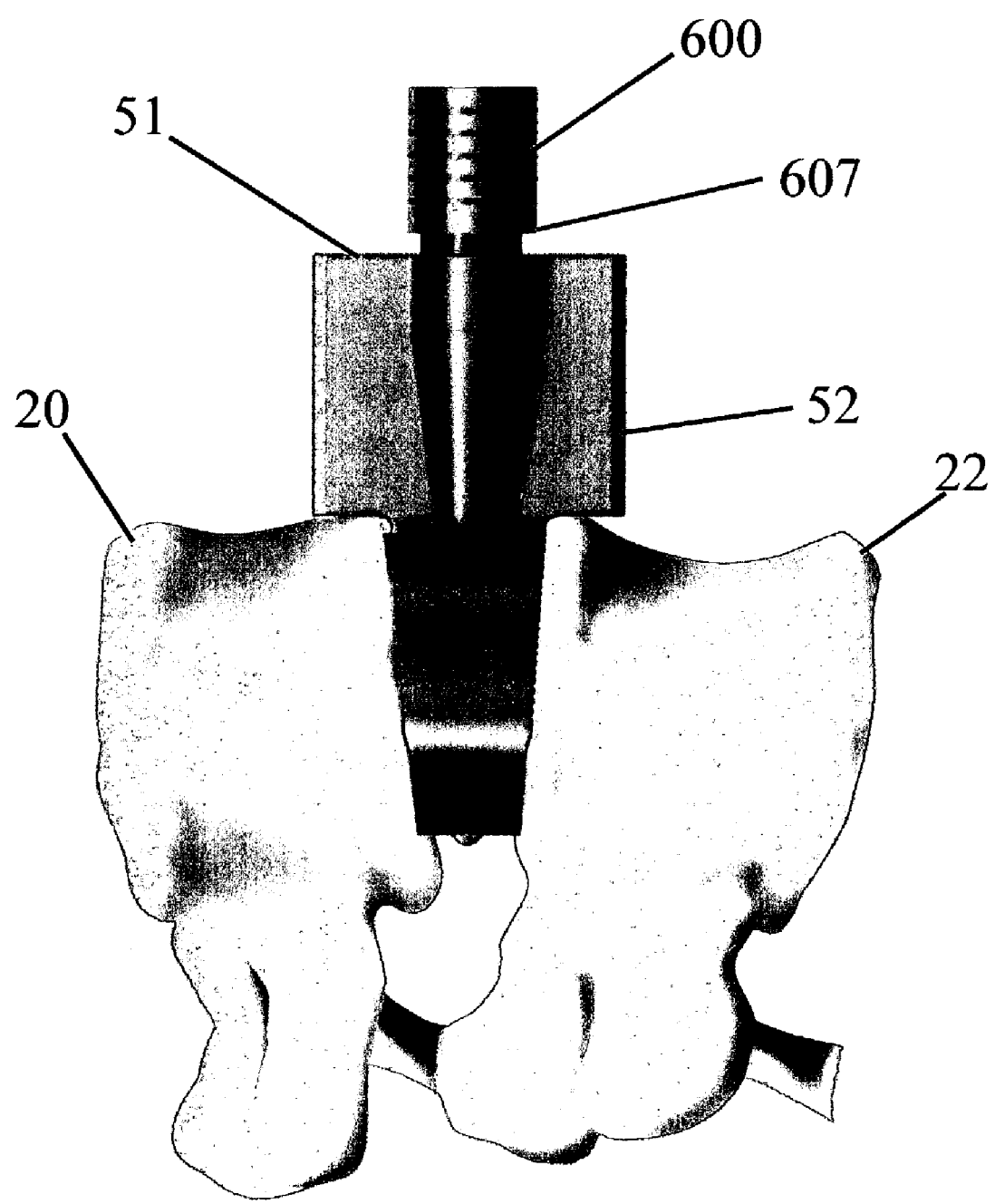
FIG. 35 shows a vertebrae preparation step using a rasp according to the principles of the present invention.

After the wedge distractor 50 has been removed, a rasp 600 of the appropriate size is selected. The end plates 20', 22' are then prepared by inserting the head of the rasp through the portal 52 and rasping in an anterior/posterior direction. Preferably, the rasp 600 is advanced until shoulder 607 of the rasp is adjacent the posterior most edge 51 of the portal 52 (see FIG. 35). In this position, the thickness of the rasp head is slightly larger (e.g., about one-half millimeter) than the portal paddles. In this manner, the rasp prepares the first regions 24 of the end plates 20', 22' as shown in FIG. 9A. Fluoroscopy can be used to ensure proper placement of the rasp within the disc space.

Once the end plates 20', 22' have been prepared with the rasp as indicated above, a box chisel 510 of the appropriate size is preferably selected. Box chisel 510 is then inserted over the shaft 603 of the rasp 600. Rotational alignment between the rasp 600 and the chisel 510 is provided by the pin 703 of side handle 701 (see FIG. 13).

Figure 36:
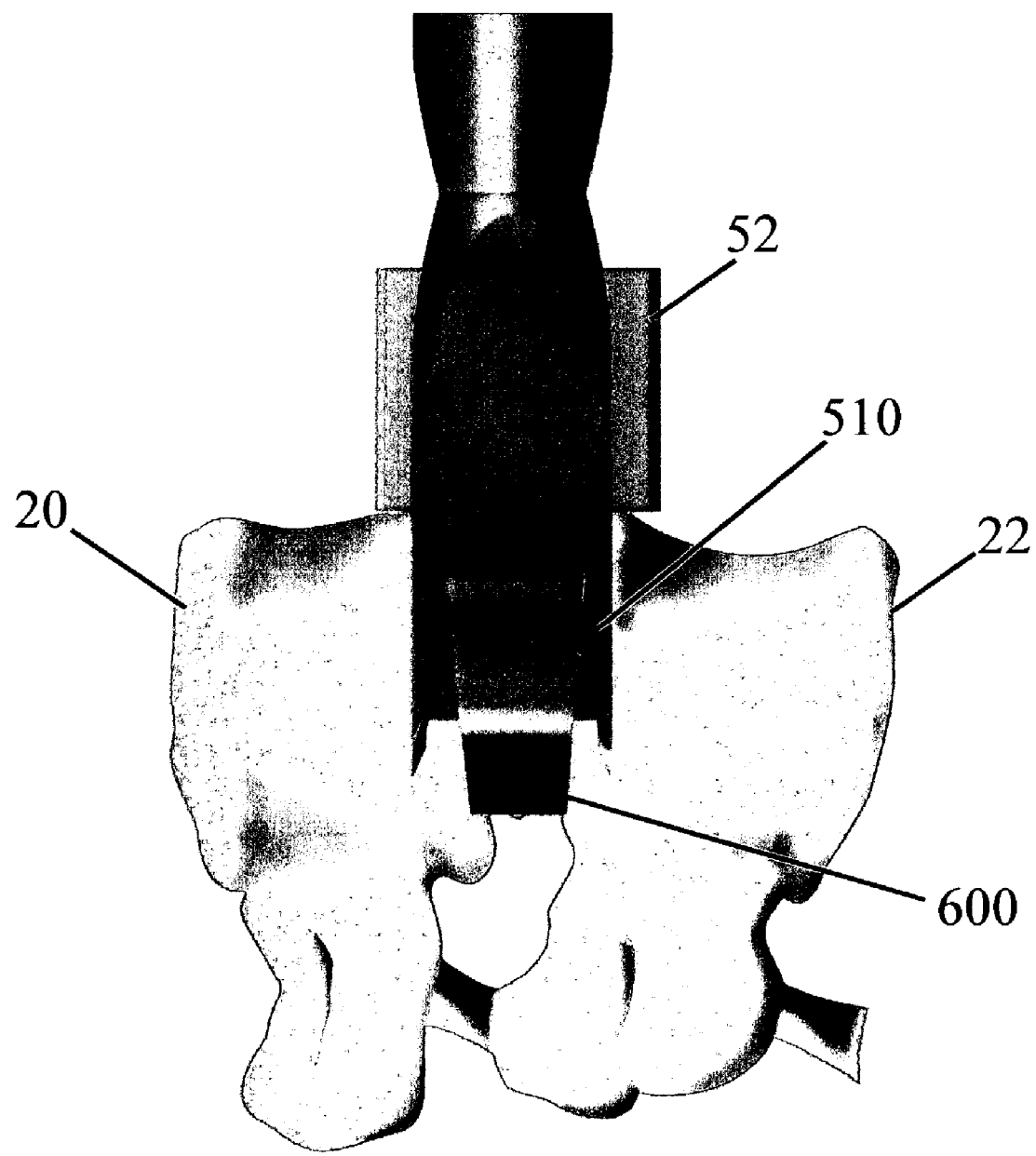
FIG. 36 shows a vertebrae preparation step using a box chisel according to the principles of the present invention.

When rotational alignment between the rasp 600 and the box chisel 510 achieved, the chisel 510 is slid along the shaft 603 of the rasp toward the vertebrae 20, 22. The chisel 510 is then impacted (e.g., with slap hammer 501) against the vertebrae 20, 22 until edges 522 and 523 of the chisel 510 contact the back side 617 (shown in FIG. 15) of the rasp head (see FIG. 36). Thereafter, the rasp 600 and chisel 510 combination can be removed from the intervertebral space using the slap hammer 501.

Figure 37:
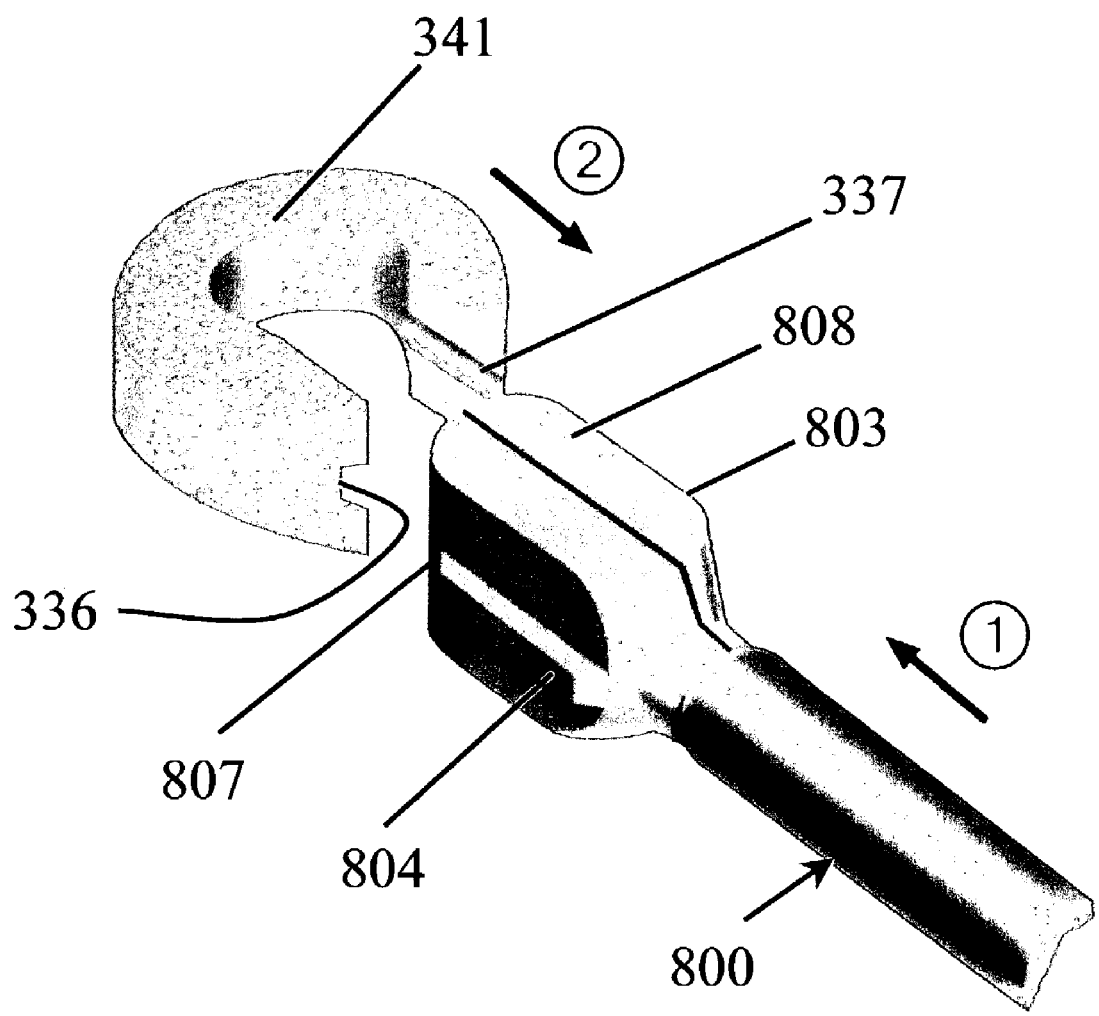
FIG. 37 is a perspective view of a support member being positioned upon an insertion tool according to the principles of the present invention.

After the rasp 600 and box chisel 510 have been removed, an insertion head 803 having a size corresponding to the size of the rasp 600 and chisel 510 is selected. The insertion sleeve 820 is placed over the shaft of the insertion tool 800 and slid toward the insertion head 803 causing the arms 807, 808 of the insertion head 803 to be flexed together. Thereafter, the support member 341 of the implant 320 is inserted onto the insertion head 803 such that tabs 804, 805 of the insertion head fit within the corresponding grooves 336, 337 of the support member 341 (see FIG. 37). The sleeve 820 is then slid away from the insertion head 803 and threaded on the handle 850 of the insertion tool 800. With the sleeve 820 pulled back, the arms 807, 808 of the insertion head flex outwardly to securely hold the support member 341 on the insertion head.

Figure 38:
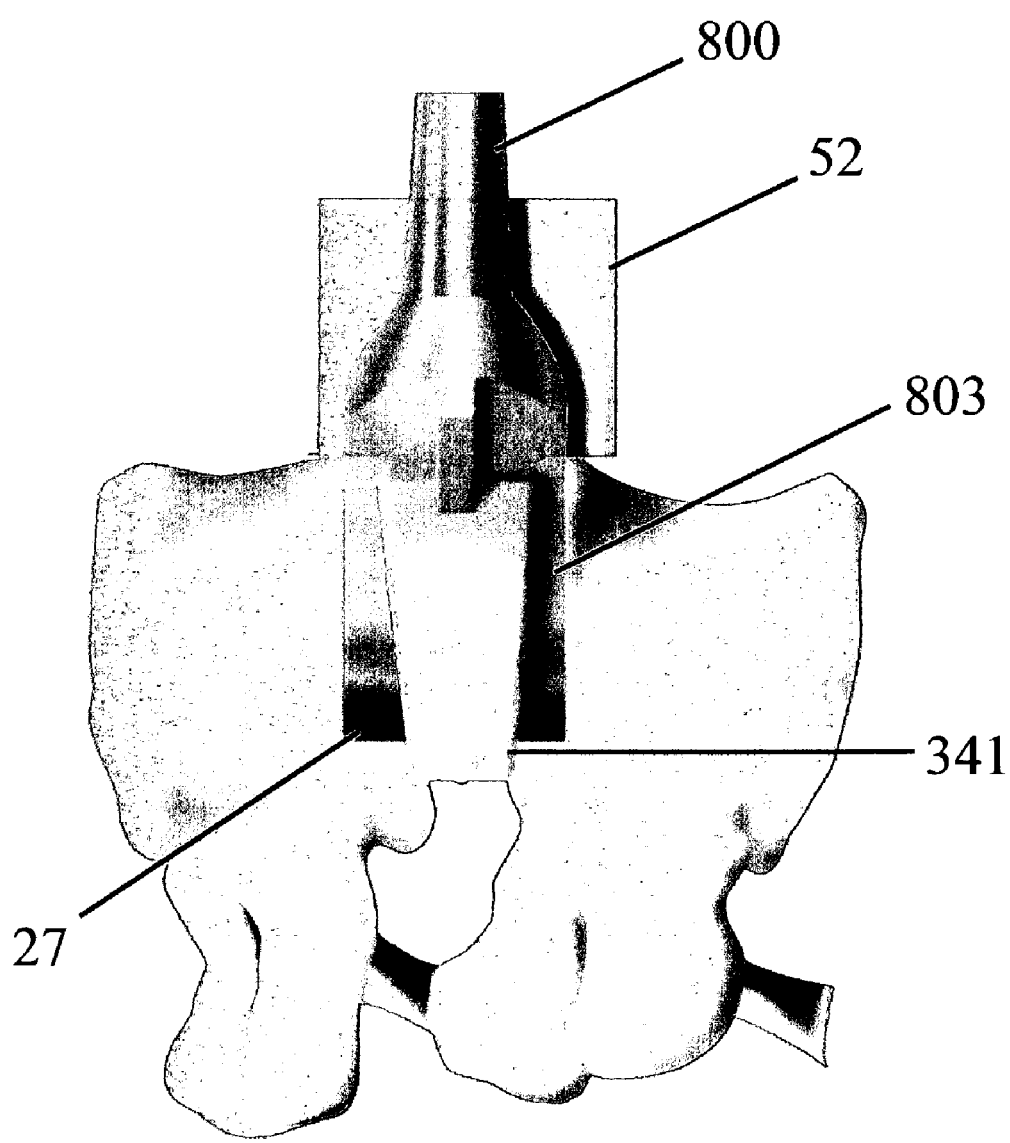
FIG. 38 shows a support member insertion step according to the principles of the present invention.

The insertion tool 800 is then used to insert the support member 341 through the portal 52 into the intervertebral space between the vertebrae 20, 22. Light impaction may be utilized to deliver the support member 341 into its final position. Final positioning is achieved when the insertion head contacts a positive stop 27 formed in the vertebrae 20, 22 by the chisel 510 (see FIG. 38). Thereafter, the inserter sleeve 820 is unthreaded from the inserter handle 850 and pushed toward the inserter head 803 to release the inserter head 803 from the support member 341. The insertion tool 800 is then removed from the support member 341 leaving the support member 341 within the intervertebral space.

Figure 39:
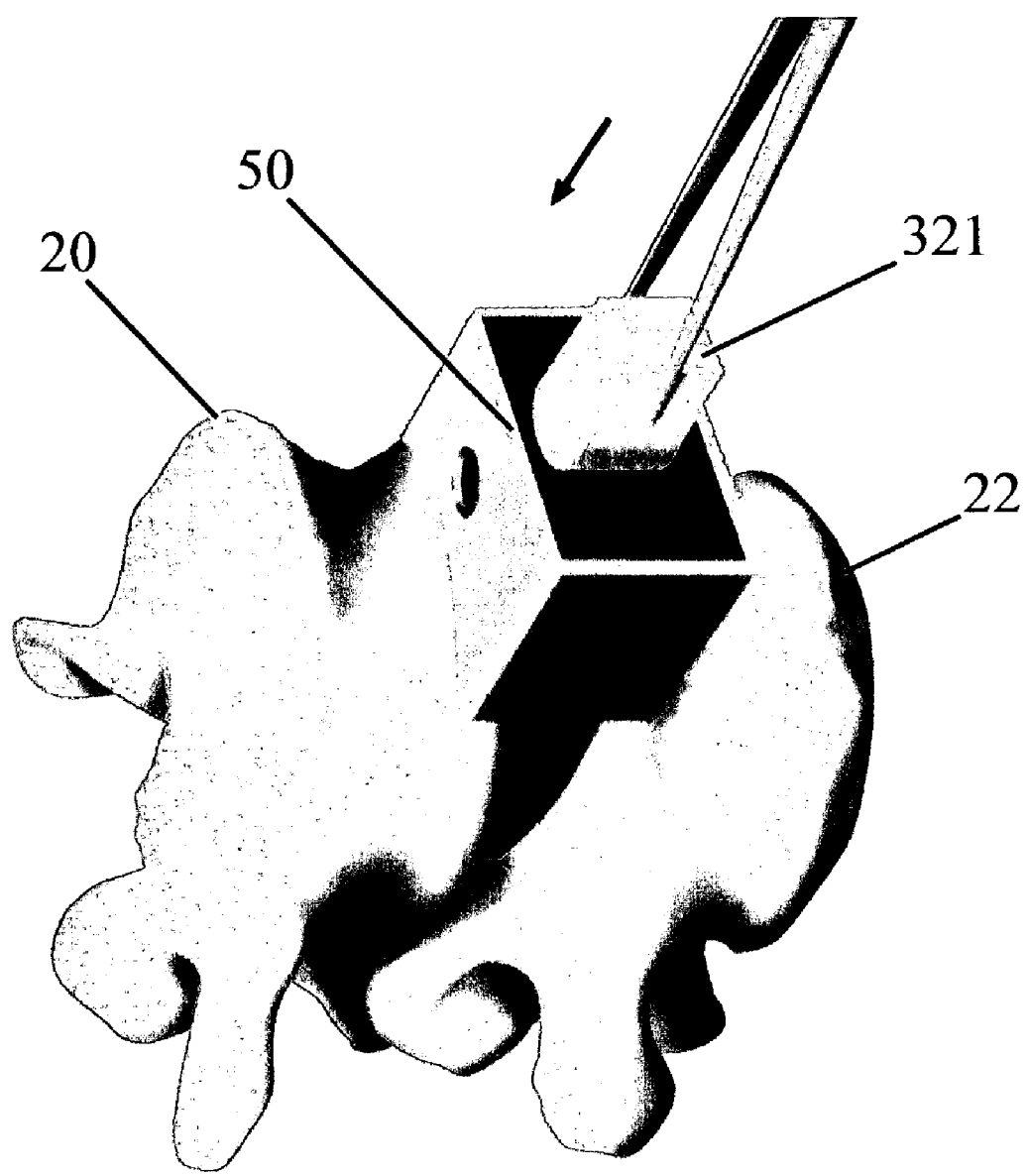
FIG. 39 is shows a growth member insertion step according to the principles of the present invention.
Figure 40:
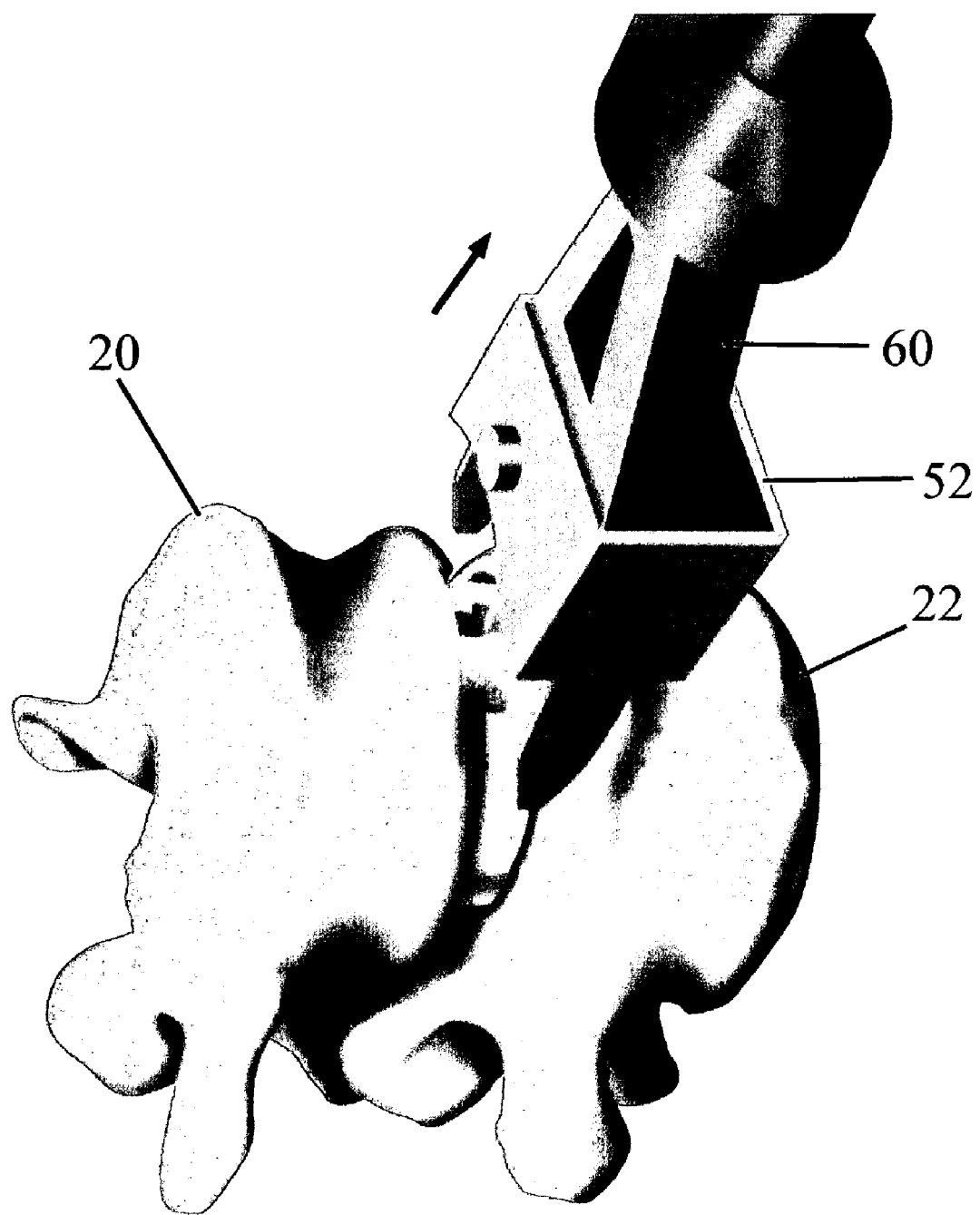
FIG. 40 shows a portal extraction step according to the principles of the present invention.
Figure 41:
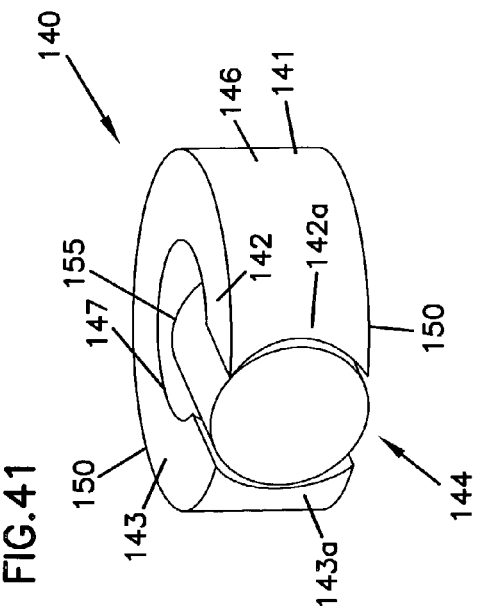
FIG. 41 is a perspective view of an implant that is another embodiment of the present invention.
Figure 42:
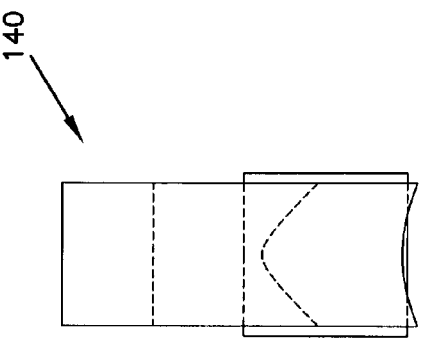
FIG. 42 is a side elevational view of the implant of FIG. 41.
Figure 43:
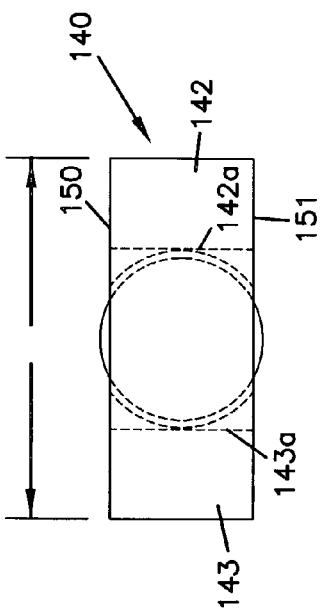
FIG. 43 is a front elevational view of the implant of FIG. 41.
Figure 44:
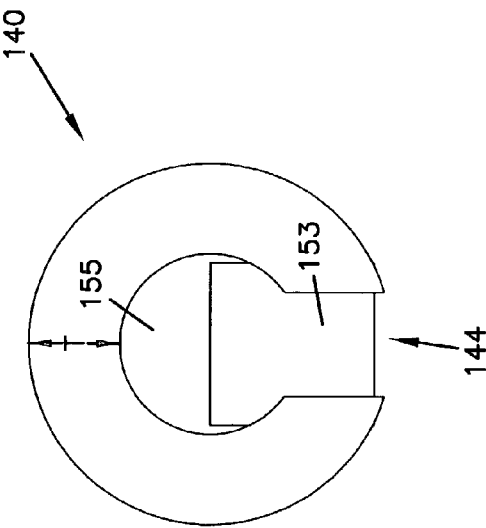
FIG. 44 is a top plan view of the implant of FIG. 41.

After the support member 341 has been implanted, a growth member 321 having a size that corresponds to the support member 341 is selected. Preferably, the growth member 321 has a height that is at least two millimeters, and preferably about three millimeters larger than the corresponding support member 341. A tool such as a forceps 29 is used to place the growth member 321 into the channel (i.e., region 26 shown in FIGS. 10B–12) created by the chisel 510 (see FIG. 39). A tamp can be used to tap the growth member into the channel. Once the growth member 321 is in its final position, the portal extractor 60 is used to remove the portal 52 as shown in FIG. 40. The procedure is then finalized by conducting conventional surgical closure and post-operative care procedures.

V. Alternative Implant Configuration

FIGS. 41–44 illustrate an alternative embodiment of an implant 140. According to this embodiment, implant 140 includes a body 141 having a "C-shaped" configuration comprising a first arm 142 continuous with a second arm 143 forming a space 144 therebetween. Body 141 also includes an external wall 146 and an internal wall 147. As best illustrated in FIGS. 8a and 8c, the facing surfaces of arms 142 and 143 are concave 142a, 143a, respectively. First bearing surface 150 and second bearing surface 151 are planar. However, in an alternative embodiment, one or both of bearing surfaces 150 and 151 could be configured as described for implants 70, 80 or 100.

A central void 155 is bounded by inner wall 147 and is continuous with opening 144 between arms 142 and 143. Thus, body 141 is a support component which can receive a growth component 153 in central void 155. In the illustrated embodiment, growth component 153 can be a dowel of cancellous bone.

The implants described herein can be included in a kit comprising a plurality of incrementally sized implants which can be selected for use by the clinician based on the size needed for a particular patient. In other embodiments, kits will be provided which include instrumentation for performing an implant procedure with or without a plurality of incrementally sized implants. Further, surface preparation tools (e.g., rasps and cutting tools) other than those specifically depicted herein can be used to practice various aspects of the invention.

Having now described the present invention, it will be apparent to one of ordinary skill in the art that many changes and modifications can be made in the invention without departing from the spirit or scope of the appended claims.

We claim:

1. A bone implant comprising:
    a support member sized for intervertebral implantation, the support member defining a cavity having an open end positioned opposite from a closed end; and
    a growth member sized to be inserted into the cavity of the support member through the open end of the cavity after implantation of the support member into an intervertebral space, the growth member having a pre-manufactured shape that generally complements a shape of the cavity,
    wherein the growth member includes oppositely positioned bone engagement surfaces separated by a thickness, and wherein the growth member also includes planar side wall surfaces that extend between the bone engagement surfaces.

2. The bone implant of claim 1 wherein the open end of the cavity and the growth member are relatively sized such that the growth member can be inserted into the cavity through the open end without requiring expansion of the support member.

3. The bone implant of claim 1, wherein the support member includes cortical bone and the growth member includes cancellous bone.

4. The bone implant of claim 1, wherein the growth member comprises an osteoconductive insert block.

5. The bone implant of claim 4, wherein the open end of the cavity has a width along a direction, and the cavity has an internal dimension along the direction, the internal dimension being greater than the width of the open end.

6. The bone implant of claim 5, wherein the bone engagement surfaces are planar.

7. The bone implant of claim 6, wherein the side wall surfaces are generally perpendicular relative to the bone engagement surfaces.

8. The bone implant of claim 5, wherein the insert block includes a first end positioned opposite from a second end, the first end including a nose having a curvature that generally matches a curvature of the curved inner wall of the cavity.

9. The bone implant of claim 8, wherein the insert block includes substantially parallel sidewall surfaces that extend between the first and second ends.

10. The bone implant of claim 9, wherein the second end of the insert block includes a substantially planar surface that extends between the sidewall surfaces.

11. The bone implant of claim 10, wherein the substantially planar surface is generally perpendicular relative to the sidewall surfaces.

12. The bone implant of claim 8, wherein the insert block includes substantially parallel bone engagement surfaces that extend between the first and second ends.

13. The bone implant of claim 5, wherein the growth member is non-threaded.

14. The bone implant of claim 4, wherein the insert block includes oppositely positioned planar bone engagement surfaces.

15. The bone implant of claim 4, wherein the cavity of the support member is defined by opposing inner wall surfaces that extend from the open end of the cavity toward to closed end of the cavity, and wherein the closed end of the cavity is defined by a curved inner wall surface that extends between the opposing inner wall surfaces.

16. The bone implant of claim 1, wherein the growth member is non-threaded.

17. A bone implant comprising:
 a support member size for intervertebral implantation, the support member defining a cavity having an open end positioned opposite from a closed end; and
 a growth member sized to be inserted into the cavity of the support member through the open end of the cavity after implantation of the support member into an intervertebral space, the growth member having a pre-manufactured shape that generally complements a shape of the cavity,
wherein the support member includes oppositely positioned load bearing surfaces separated by a thickness, wherein the growth member includes oppositely positioned bone engagement surfaces separated by a thickness, and wherein the thickness of the growth member is greater than the thickness of the support member.

18. The bone implant of claim 17, wherein the thickness of the support member varies such that the support member has a wedge shape.

19. The bone implant of claim 18, wherein the thickness of the growth member is substantially constant.

20. The bone implant of claim 19, wherein the thickness of the support member is larger adjacent the open end of the cavity than adjacent the closed end of the cavity.

21. The bone implant of claim 17, wherein the growth member is non-threaded.

22. An implant comprising
 a partial cortical ring defining an inner pocket, the partial cortical ring having a thickness defined between first and second load bearing surfaces, the inner pocket being open adjacent the first and second load bearing surfaces, the partial cortical ring also defining a radial opening for providing access to the inner pocket, the radial opening being positioned opposite from a closed end of the inner pocket;
 a non-threaded cancellous insert block having a pre-manufactured shape that complements the shape of the inner pocket, the insert block being insertable into inner pocket through the radial opening, the insert block having a thickness defined between first and second bone engagement surfaces, the thickness of the insert block being greater than the thickness of the partial cortical ring.

* * * * *

UNITED STATES PATENT AND TRADEMARK OFFICE
CERTIFICATE OF CORRECTION

| | | |
|---|---|---|
| PATENT NO. | : 7,018,416 B2 | Page 1 of 1 |
| APPLICATION NO. | : 10/080375 | |
| DATED | : March 28, 2006 | |
| INVENTOR(S) | : David A. Hanson | |

It is certified that error appears in the above-identified patent and that said Letters Patent is hereby corrected as shown below:

In claim 15, column 17, line 28, change "toward to closed" to --toward the closed--.

In claim 22, column 18, line 21, change "An implant comprising" to --An implant comprising:--, as shown in orginal claim 19 (now claim 22) in the specification on page 29, line 10.

Signed and Sealed this

Nineteenth Day of September, 2006

JON W. DUDAS
*Director of the United States Patent and Trademark Office*